(12) United States Patent
Okada et al.

(10) Patent No.: US 9,080,988 B2
(45) Date of Patent: Jul. 14, 2015

(54) FOREIGN MATTER SENSING DEVICE AND NON-CONTACT ELECTRIC-POWER TRANSFER SYSTEM

(71) Applicant: DENSO CORPORATION, Kariya, Aichi-pref. (JP)

(72) Inventors: Hiroki Okada, Chiryu (JP); Takayoshi Honda, Nagoya (JP)

(73) Assignee: DENSO CORPORATION, Kariya (JP)

( * ) Notice: Subject to any disclaimer, the term of this patent is extended or adjusted under 35 U.S.C. 154(b) by 167 days.

(21) Appl. No.: 13/826,151

(22) Filed: Mar. 14, 2013

(65) Prior Publication Data
US 2013/0241476 A1    Sep. 19, 2013

(30) Foreign Application Priority Data
Mar. 15, 2012  (JP) .................................. 2012-58220

(51) Int. Cl.
| | |
|---|---|
| G01N 21/94 | (2006.01) |
| B60L 11/00 | (2006.01) |
| B60L 11/18 | (2006.01) |
| H02J 7/02 | (2006.01) |

(52) U.S. Cl.
CPC ............. *G01N 21/94* (2013.01); *B60L 11/005* (2013.01); *B60L 11/182* (2013.01); *B60L 11/1833* (2013.01); *B60L 11/1835* (2013.01); *B60L 11/1864* (2013.01); *B60L 11/1877* (2013.01); *B60L 2210/30* (2013.01); *B60L 2210/40* (2013.01); *B60L 2240/36* (2013.01); *B60L 2250/10* (2013.01); *H02J 7/025* (2013.01); *Y02T 10/7005* (2013.01); *Y02T 10/7022* (2013.01); *Y02T 10/7061* (2013.01); *Y02T 10/7241* (2013.01); *Y02T 90/12* (2013.01); *Y02T 90/121* (2013.01); *Y02T 90/122* (2013.01); *Y02T 90/125* (2013.01); *Y02T 90/127* (2013.01); *Y02T 90/14* (2013.01)

(58) Field of Classification Search
CPC ........................... Y02T 90/122; B60L 11/182
USPC ........................................................ 320/108
See application file for complete search history.

(56) References Cited

U.S. PATENT DOCUMENTS

| | | | |
|---|---|---|---|
| 2005/0178632 A1* | 8/2005 | Ross | 191/10 |
| 2010/0156346 A1* | 6/2010 | Takada et al. | 320/108 |
| 2010/0161216 A1* | 6/2010 | Yamamoto | 701/207 |
| 2011/0074346 A1* | 3/2011 | Hall et al. | 320/108 |

(Continued)

FOREIGN PATENT DOCUMENTS

| | | |
|---|---|---|
| JP | 2007-267578 | 10/2007 |
| JP | 2010-252498 | 11/2010 |

(Continued)

*Primary Examiner* — Samuel Berhanu
*Assistant Examiner* — Jerry D Robbins
(74) *Attorney, Agent, or Firm* — Nixon & Vanderhye PC

(57) ABSTRACT

A foreign matter sensing device includes a first determiner that determines whether there is a foreign matter in a foreign matter detection range based on an image imaged by an imaging portion, and a second determiner that determines whether there is a foreign matter in the foreign matter detection range based on a temperature sensed by a temperature sensor. The second determiner executes determining whether there is a foreign matter in the foreign matter detection range while electric-power is transferred between a vehicle-side coil and an out-of-vehicle coil, when the first determiner determines that there is no foreign matter after the imaging portion images the image of the foreign matter detection range in response to a start demand instructing to start transferring electric-power.

23 Claims, 24 Drawing Sheets

(56) References Cited

U.S. PATENT DOCUMENTS

2011/0254503 A1* 10/2011 Widmer et al. ............... 320/108
2011/0285349 A1* 11/2011 Widmer et al. ............... 320/108
2011/0316553 A1* 12/2011 Taguchi et al. ............... 324/500

FOREIGN PATENT DOCUMENTS

| JP | 2011-229264 | 11/2011 |
| JP | 2012-257404 | 12/2012 |
| JP | 2013-046492 | 3/2013 |

* cited by examiner

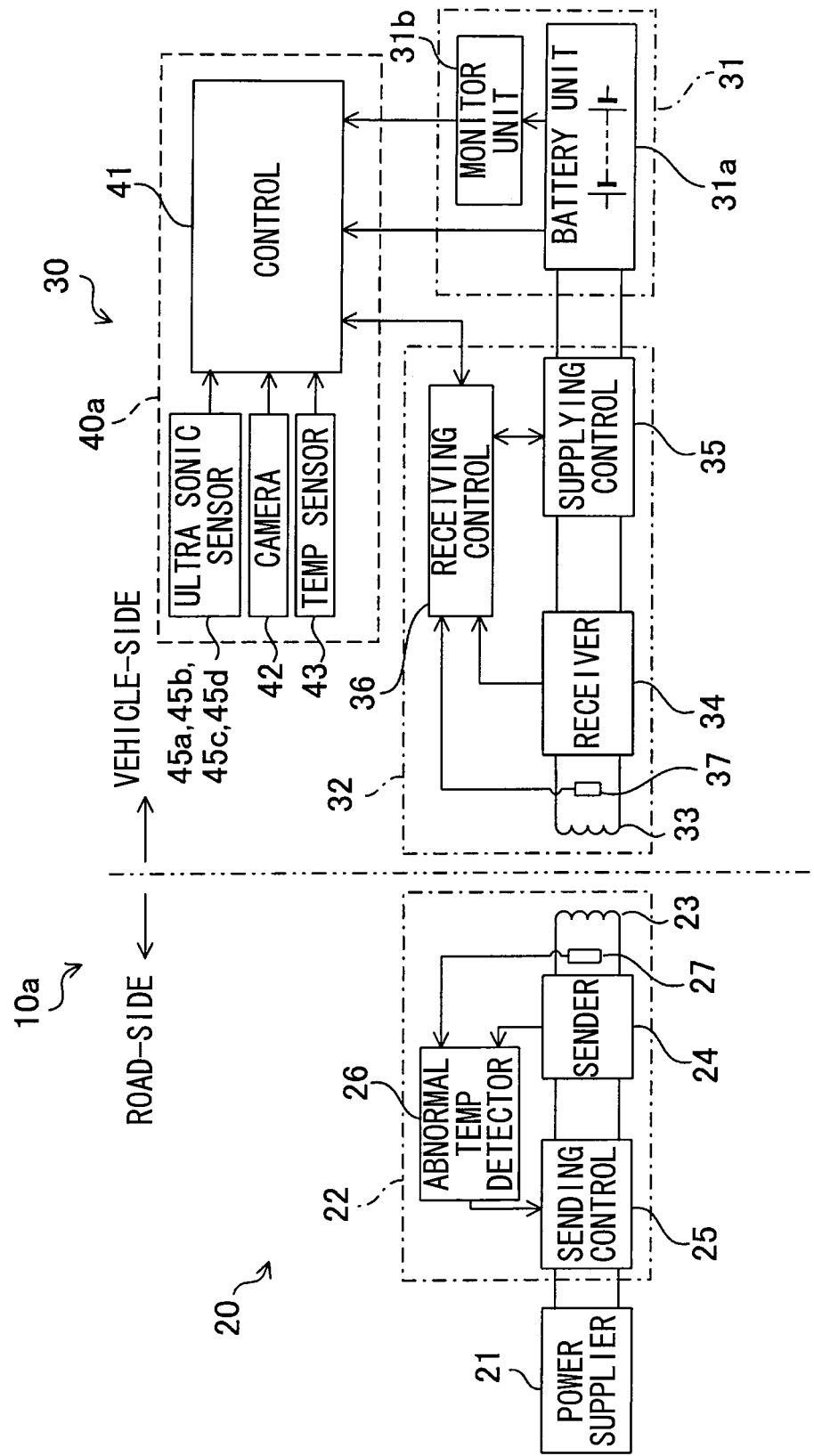

US 9,080,988 B2

FOREIGN MATTER SENSING DEVICE AND NON-CONTACT ELECTRIC-POWER TRANSFER SYSTEM

CROSS REFERENCE TO RELATED APPLICATION

This application is based on Japanese Patent Application No. 2012-58220 filed on Mar. 15, 2012, the disclosure of which is incorporated herein by reference in its entirety.

TECHNICAL FIELD

The present disclosure relates to a foreign matter sensing device and a non-contact electric-power transfer system.

BACKGROUND

JP-2007-267578A describes an energy transfer device which charges a vehicle battery using microwave and an object detecting device which detects a foreign matter located between a power-sending coil and a power-receiving coil in the energy transfer device. The object detecting device includes a camera which images a space between the power-sending coil and the power-receiving coil, and a processor which processes the image data taken by the camera so as to detect a foreign matter as an obstacle. If it is determined that there is an obstacle, the processor stops sending the microwave. Thus, energy loss caused by the obstacle can be avoided, and the irradiation of the microwave to the obstacle can be stopped.

However, it is required to keep a predetermined brightness for the space between the power-sending coil and the power-receiving coil in order to take the image with the camera. Therefore, lighting is continuously needed in night, because it is dark around the space at night, while detecting a foreign matter.

SUMMARY

According to a first example of the present disclosure, a foreign matter sensing device that detects a foreign matter located between a vehicle-side coil, which is used when a battery mounted to a vehicle is charged and discharged, and an out-of-vehicle coil which transfers electric-power with the vehicle-side coil in non-contact state includes an imaging portion, a first determiner, a temperature sensor, and a second determiner. The imaging portion images an image of a foreign matter detection range above the out-of-vehicle coil. The first determiner determines whether there is a foreign matter in the foreign matter detection range based on the image imaged by the imaging portion. The temperature sensor senses a temperature of the foreign matter detection range. The second determiner determines whether there is a foreign matter in the foreign matter detection range based on the temperature sensed by the temperature sensor. The second determiner executes determining whether there is a foreign matter in the foreign matter detection range while electric-power is transferred between the vehicle-side coil and the out-of-vehicle coil, when the first determiner determines that there is no foreign matter after the imaging portion images the image of the foreign matter detection range in response to a start demand instructing to start transferring electric-power.

According to a second example of the present disclosure, a non-contact electric-power transfer system includes the foreign matter sensing device, the out-of-vehicle coil, and a control part that controls the non-contact electric-power transfer using the battery through the out-of-vehicle coil and the vehicle-side coil.

BRIEF DESCRIPTION OF THE DRAWINGS

The above and other objects, features and advantages of the present disclosure will become more apparent from the following detailed description made with reference to the accompanying drawings. In the drawings:

FIG. 16 is a block diagram illustrating an electric structure of a foreign matter sensing device and a non-contact electric-power transfer system according to a fifth embodiment;

DETAILED DESCRIPTION

Figure 1:
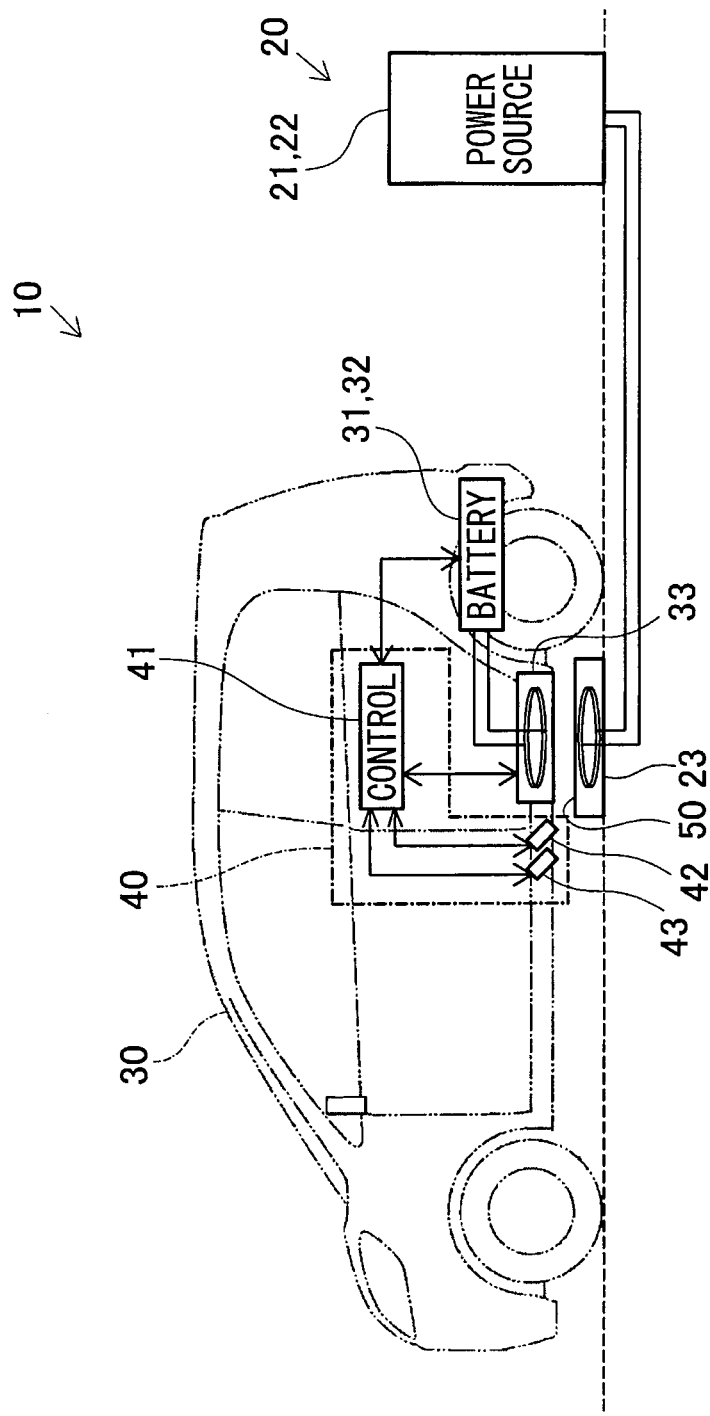
FIG. 1 is a block diagram illustrating a foreign matter sensing device and a non-contact electric-power transfer system according to a first embodiment.

Embodiments of the present disclosure will be described hereafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

(First Embodiment)

Figure 2:
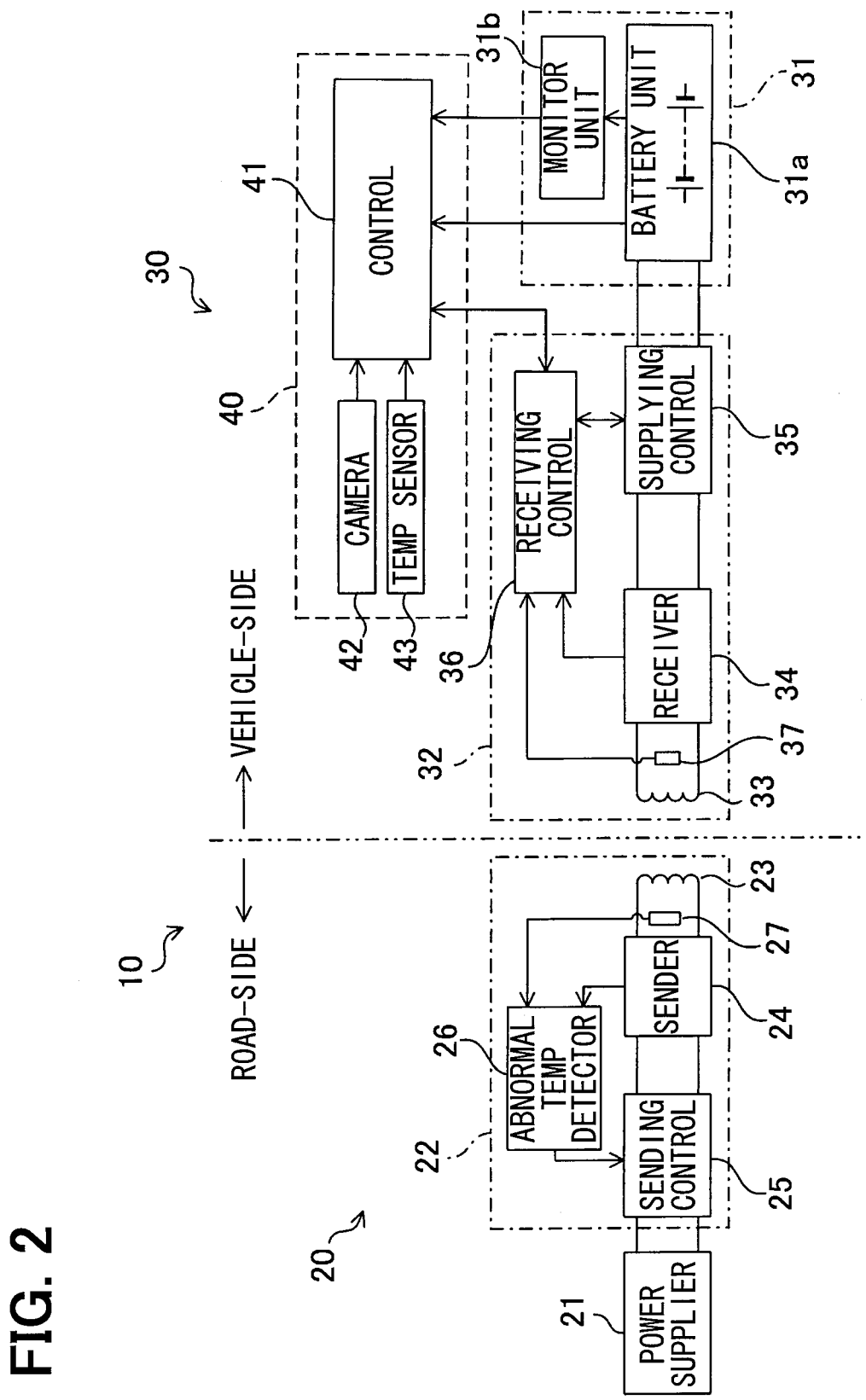
FIG. 2 is a block diagram illustrating an electric structure of the foreign matter sensing device and the non-contact electric-power transfer system of the first embodiment.

A foreign matter sensing device 40 and a non-contact electric-power transfer system 10 according to a first embodiment are explained with reference to FIGS. 1-3.

The non-contact electric-power transfer system 10 is defined between a non-contact electric-power transfer equipment 20 installed in a predetermined parking space and a vehicle 30 such as electric car. A power source 21 of the non-contact electric-power transfer equipment 20 sends or receives electric-power in non-contact state to a battery equipment 31 mounted to the vehicle 30 as a power source. Electric-power is transferred between an out-of-vehicle coil 23 of the non-contact electric-power transfer equipment 20 and a vehicles-side coil 33 of the vehicle 30. More specifically, the non-contact electric-power transfer (electric-power transmission) between the power source 21 and the battery equipment 31 is realized by producing an electric-power transmission transformer by electromagnetically combining the out-of-vehicle coil 23 and the vehicle-side coil 33.

The non-contact electric-power transfer equipment 20 is explained with reference to FIG. 2.

The non-contact electric-power transfer equipment 20 has the power source 21 and an electric-power transmit equipment 22. The power source 21 sends and receives required electric power to the vehicle 30. The electric-power transmit equipment 22 carries out the non-contact electric-power transfer using the power source 21. The electric-power transmit equipment 22 has the out-of-vehicle coil 23, a power sending part 24, a power sending control part 25, and an abnormal temperature detecting element 26. The electric-power transmit equipment 22 may be separated from the out-of-vehicle coil 23, and may correspond to a control part.

The out-of-vehicle coil 23 is a coil which functions as an antenna for sending power, and is constructed to transfer electric-power with the power sending part 24. The out-of-vehicle coil 23 is arranged under the road surface to oppose the vehicle-side coil 33 which is arranged on the bottom of the vehicle 30 when the vehicle 30 is parked at a predetermined parking space by the user such as driver using the non-contact electric-power transfer system 10.

The power sending part 24 is controlled by the power sending control part 25, and supplies electric power to the out-of-vehicle coil 23 with a predetermined alternating current voltage from the power source 21. Specifically, the power sending part 24 is constructed to include a first power transmission driver driving an end of the out-of-vehicle coil 23, a second power transmission driver driving the other end of the out-of-vehicle coil 23, and a capacitor constructing a resonance circuit together with the out-of-vehicle coil 23, for example. Thereby, the power sending part 24 generates and supplies the alternating current voltage with the predetermined frequency to the out-of-vehicle coil 23. The first and second power transmission driver may be made of an inverter circuit (buffer circuit) constructed by a power MOS transistor, for example.

The abnormal temperature detecting element 26 detects the temperature around the out-of-vehicle coil 23 based on a temperature signal output from a thermistor 27 which is placed around the out-of-vehicle coil 23, and sends an abnormal temperature signal to the power sending control part 25 when the detected temperature is larger than or equal to an abnormal temperature. When the abnormal temperature signal is received by the power sending control part 25, the power sending control part 25 controls the power sending part 24 to stop supplying electricity to the out-of-vehicle coil 23.

When the user performs a predetermined operation to an operation part (not shown) to start charging, the non-contact electric-power transfer equipment 20 becomes to be able to conduct the non-contact electric-power transfer through the out-of-vehicle coil 23 to the battery equipment 31 of the vehicle 30 parked or stopped at the parking space.

Next, the construction on the side of the vehicle 30 is explained hereinafter.

The battery equipment 31, an electric-power transfer equipment 32, and the foreign matter sensing device 40 are mounted to the vehicle 30. The battery equipment 31 has a secondary rechargeable battery unit 31a constructed by a lithium ion battery (LiB), and a monitoring unit 31b which monitors battery state such as electric-power transfer amount of the battery unit 31a. The battery equipment 31 may be made of other battery different from the lithium ion battery, for example, a lead battery may be adopted as the battery unit 31a. The rechargeable battery unit 31a may be replaced with a capacitor such as lithium ion capacitor (LiC) or electric double layer capacitor (EDLC).

The electric-power transfer equipment 32 conducts the non-contact electric-power transfer using the battery equipment 31 on the side of the vehicle 30. The electric-power transfer equipment 32 supplies the electric power from the non-contact electric-power transfer equipment 20 to the battery equipment 31, and supplies electric power to an external equipment including the non-contact electric-power transfer equipment 20 through the vehicle-side coil 33 from the battery equipment 31. The electric-power transfer equipment 32 has the vehicle-side coil 33, a power receiving part 34, a power supplying control part 35, and a power receiving control part 36.

The vehicle-side coil 33 is a coil which functions as an antenna for receiving power or an antenna for sending power, and is constructed to transfer electric-power with the power receiving part 34. The vehicle-side coil 33 is arranged on the bottom of the vehicle 30 to oppose the out-of-vehicle coil 23 disposed under the road surface when the vehicle 30 is parked at the predetermined parking space to which the non-contact electric-power transfer equipment 20 is mounted.

The power receiving part 34 is equipped with a rectification circuit, and converts the alternating current induced voltage produced in the vehicle-side coil 33 into direct-current voltage and outputs the direct-current voltage. Moreover, the power receiving part 34 is constructed to have similar function as the power sending part 24 when the electric-power transfer equipment 32 functions as an electric-power transfer portion to supply electric power to an external equipment through the vehicle-side coil 33 from the battery equipment 31.

The power supplying control part 35 generates the power supply voltage by adjusting the voltage level of the direct-current voltage converted in the power receiving part 34, and supplies the voltage to the rechargeable battery unit 31a of the battery equipment 31. Moreover, the power supplying control part 35 is constructed to have similar function as the power sending control part 25 when the electric-power transfer equipment 32 functions as an electric-power transfer portion to supply electric power to an external equipment through the vehicle-side coil 33 from the battery equipment 31.

The power receiving control part 36 manages overall control of the electric-power transfer equipment 32, and controls the power supplying control part 35 according to the direct-current voltage which is converted by the power receiving part 34. Moreover, the power receiving control part 36 detects the temperature around the vehicle-side coil 33 based on the temperature signal output from a thermistor 37 arranged around the vehicle-side coil 33, and stops the non-contact electric-power transfer using the battery equipment 31 when the detected temperature is higher than or equal to an abnormal temperature. Moreover, the power receiving control part 36 stops the non-contact electric-power transfer using the battery equipment 31 according to a foreign matter detection signal transmitted from the foreign matter sensing device 40.

The electric-power transfer equipment 32 becomes to conduct the non-contact electric-power transfer through the vehicle-side coil 33 when a user performs a predetermined operation to an operation part (not shown) provided in the vehicle 30 to start charging in the state where the vehicle 30 is parked or stopped at the parking space, and when the operation information is inputted into the power receiving control part 36. The operation information is constructed to be inputted into the foreign matter sensing device 40 as a start demand starting the non-contact electric-power transfer. In addition, the start demand may be inputted directly from the operation part into the foreign matter sensing device 40 or may be inputted into the foreign matter sensing device 40 through the electric-power transfer equipment 32.

When the charging of the battery equipment 31 is completed, the electric-power transfer equipment 32 transmits a charging complete signal which represents that the charging was completed to the foreign matter sensing device 40. Moreover, in the case where the charging is suspended according to operation of the operation part by a user or in response to abnormalities, the electric-power transfer equipment 32 transmits a charging stop signal which represents that the charging was suspended to the foreign matter sensing device 40.

Next, the foreign matter sensing device 40 is explained.

The foreign matter sensing device 40 detects a foreign matter which intervenes between the vehicle-side coil 33 and the out-of-vehicle coil 23. The foreign matter sensing device 40 has a control part 41 which manages overall control, a camera 42, and a temperature sensor 43.

The control part 41 includes a microcomputer and memories such as ROM, RAM, or EEPROM, for example. The control part 41 performs a foreign matter detection process in which a foreign matter is detected according to the picture information inputted from the camera 42, or the temperature information inputted from the temperature sensor 43 by a predetermined computer program.

The camera 42 is arranged around the vehicle-side coil 33 integrally with the vehicle-side coil 33 so that the picture information that is an image imaging a protection surface (henceforth referred as foreign matter detection range 50) to protect the upper side of the out-of-vehicle coil 23 is outputted to the control part 41. Especially, the camera 42 is arranged so that the center of the vehicle-side coil 33 and the center of the foreign matter detection range 50 are in agreement with each other when the vehicle-side coil 33 is projected on the foreign matter detection range 50. In addition, the camera 42 may be constructed to output the picture information about the image imaging the foreign matter detection range 50 to the control part 41 according to an image direction signal inputted from the control part 41. The camera 42 may correspond to an imaging portion.

The temperature sensor 43 may be made of an infrared sensor, and is arranged around the vehicle-side coil 33 so as to detect the heat energy amount produced by heat radiated from the foreign matter detection range 50. The temperature sensor 43 outputs a temperature signal (temperature information) to the control part 41. The temperature sensor 43 may be other sensor such as thermistor other than the infrared sensor which measures the temperature of the foreign matter detection range 50.

Figure 3:
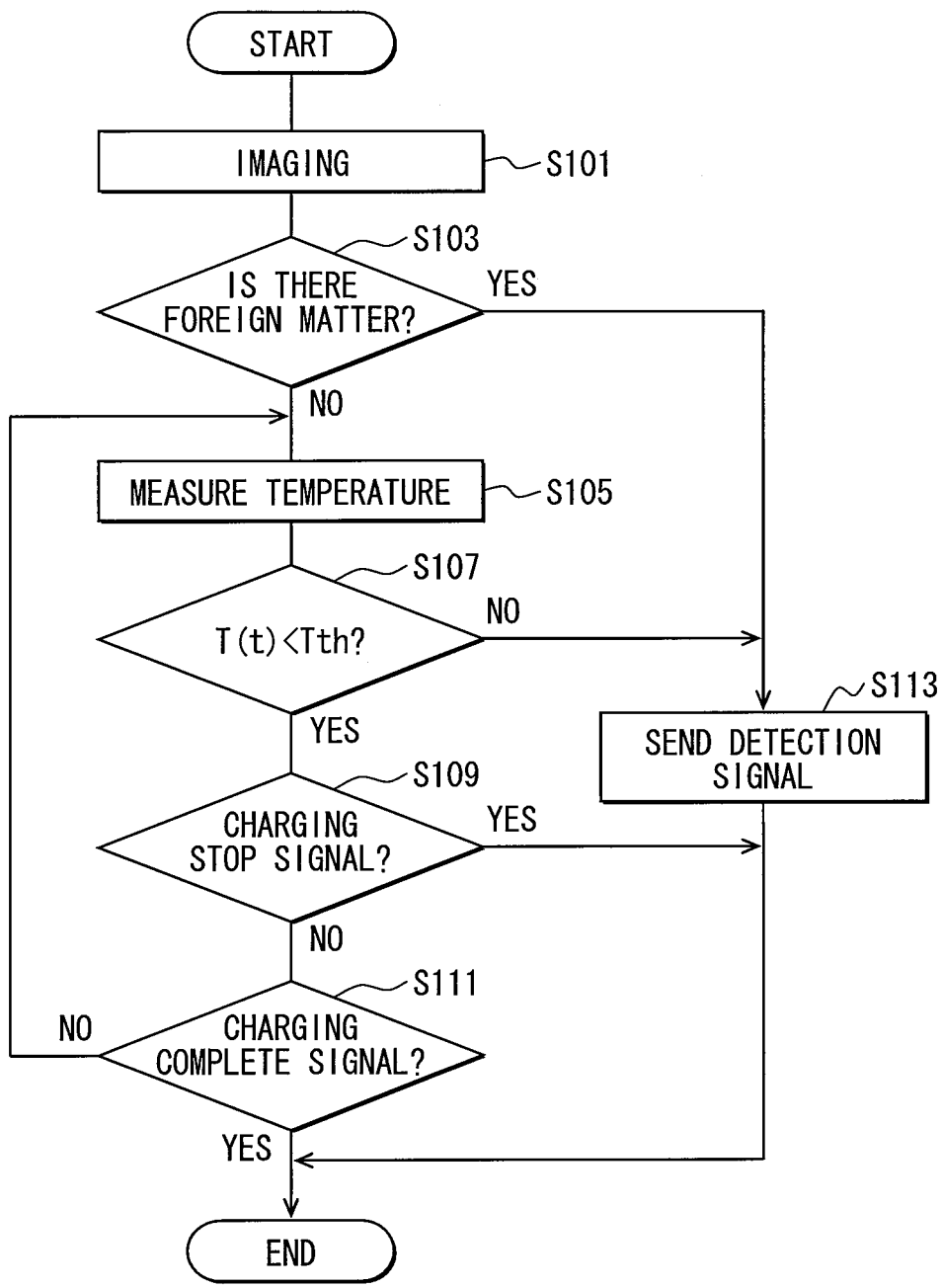
FIG. 3 is a flow chart illustrating a foreign matter detection process of the first embodiment.

Next, the foreign matter detection process carried out by the control part 41 of the foreign matter sensing device 40 is explained in detail using the flow chart shown in FIG. 3.

The vehicle 30 having the foreign matter sensing device 40 is parked or stopped to the parking space to which the non-contact electric-power transfer equipment 20 is mounted. When a user performs the predetermined operation to the operation part of the vehicle 30, the start demand starting the non-contact electric-power transfer is inputted into the control part 41 of the foreign matter sensing device 40, and the foreign matter detection process is started by the control part 41. Simultaneously, the non-contact electric-power transfer becomes possible for the electric-power transfer equipment 32 through the vehicle-side coil 33. Moreover, when a user performs a predetermined operation to the operation part of the non-contact electric-power transfer equipment 20 to start charging, the non-contact electric-power transfer becomes possible for the electric-power transfer equipment 22 through the out-of-vehicle coil 23. Thus, the non-contact electric-power transfer is executed between the out-of-vehicle coil 23 and the vehicle-side coil 33 using the power source 21, and the charging of the rechargeable battery unit 31a of the battery equipment 31 is started.

When the foreign matter detection process is started, the imaging is executed in S101 of FIG. 3. In S101, the image of the foreign matter detection range 50 is generated based on the picture information inputted from the camera 42.

Next, it is determined whether a foreign matter is included in the image at S103. When a foreign matter is not included in the image (No at S103), the imaging of the foreign matter detection range 50 using the camera 42 may be stopped for saving power consumption. The control part 41 executing S103 may be equivalent to a first determiner.

At S105, the temperature of the foreign matter detection range 50 is measured as a measurement temperature T(t) based on the temperature signal output from the temperature sensor 43. At S107, it is determined whether the measurement temperature T(t) is lower than a predetermined temperature threshold Tth. The predetermined temperature threshold Tth is a constant value which does not change according to time. The predetermined temperature threshold Tth is set with an assumption that a foreign matter (exothermic foreign matter) such as metal piece exists in the foreign matter detection range 50 and that the foreign matter generates heat according to the non-contact electric-power transfer between the out-of-vehicle coil 23 and the vehicle-side coil 33. The control part 41 executing S107 may be equivalent to a second determiner.

When the measurement temperature T(t) is lower than the temperature threshold Tth (Yes at S107), S105 and S107 are repeated until receiving the charging stop signal of S109 or the charging complete signal of S111. When the charging complete signal is received (Yes at S111) in response to the complete in the charging of the battery equipment 31 before the measurement temperature T(t) becomes higher than or equal to the temperature threshold Tth, the foreign matter detection process is completed. Moreover, when the charging stop signal is received (Yes at S109) while S105 and S107 are repeated, the foreign matter detection process is completed.

On the other hand, when the exothermic foreign matter existing in the foreign matter detection range 50 generates heat and when the measurement temperature T(t) becomes more than or equal to the temperature threshold Tth (No at S107), the foreign matter detection signal is transmitted at S113. The foreign matter detection signal representing that there is the exothermic foreign matter in the foreign matter detection range 50 is transmitted to the power receiving control part 36 of the electric-power transfer equipment 32, and the foreign matter detection process is completed.

Thus, the non-contact electric-power transfer using the battery equipment 31 is stopped when the power receiving control part 36 receives the foreign matter detection signal transmitted from the control part 41.

Moreover, also when the foreign matter is included in the image taken at S101 (Yes at S103), the foreign matter detection signal is transmitted to the power receiving control part 36 of the electric-power transfer equipment 32, and the foreign matter detection process is completed.

According to the first embodiment, the camera 42 of the foreign matter sensing device 40 images the foreign matter detection range 50 above the out-of-vehicle coil 23 according to the start demand starting the non-contact electric-power transfer. When it is determined that there is no foreign matter according to the image, a presence of a foreign matter in the foreign matter detection range 50 is determined based on the measurement temperature T(t) measured by the temperature sensor 43, while the non-contact electric-power transfer is conducted.

Thus, after it is determined that there is no foreign matter based on the image at the start time of the non-contact electric-power transfer, the determination of foreign matter is conducted using the temperature sensor 43 during the non-contact electric-power transfer. Therefore, the exothermic foreign matter in the foreign matter detection range 50 can be detected without maintaining the space between the out-of-vehicle coil 23 and the vehicle-side coil 33 bright.

Accordingly, an exothermic foreign matter can be detected without lighting the space between the out-of-vehicle coil 23 and the vehicle-side coil 33 used for the non-contact electric-power transfer.

The temperature sensor 43 is an infrared sensor which detects the infrared light emitted from the foreign matter detection range 50, so as to measures the temperature of the foreign matter detection range 50. Because the temperature of the foreign matter detection range 50 is detected in the broad area in detail, the detection precision of exothermic foreign matter can be raised.

Moreover, the non-contact electric-power transfer system 10 has the foreign matter sensing device 40, the out-of-vehicle coil 23, and the electric-power transfer equipment 22 which controls the non-contact electric-power transfer using the power source 21 through the out-of-vehicle coil 23 and the vehicle-side coil 33. Therefore, the non-contact electric-power transfer system 10 can detect an exothermic foreign matter without maintaining the brightness between the out-of-vehicle coil 23 and the vehicle-side coil 33 used for the non-contact electric-power transfer.

When a foreign matter is detected by the foreign matter sensing device 40, the non-contact electric-power transfer in the non-contact electric-power transfer system 10 is stopped by the electric-power transfer equipment 22. Therefore, the electric-power loss resulting from the foreign matter can be prevented certainly.

When the foreign matter detection signal is transmitted (i.e., when it is determined that there is an exothermic foreign matter), an alarming portion such as warning light prepared in the vehicle 30 may be actuated to notify a user of information that the charging is stopped due to an exothermic foreign matter in the foreign matter detection range 50. Therefore, the user who received the information is promoted to remove the exothermic foreign matter from the foreign matter detection range 50.

Furthermore, when it is determined that there is an exothermic foreign matter, the foreign matter detection range 50 may be imaged with the camera 42 as a foreign matter detection picture, and the foreign matter detection picture may be included in the information. Specifically, the foreign matter detection picture can be displayed on a display part (not shown) of the non-contact electric-power transfer equipment 20 which received the information from the foreign matter sensing device 40, for example. Thereby, the detection state of exothermic foreign matter can be reported visually to the user who received the information, and then the exothermic foreign matter can be removed easily.

(Second Embodiment)

Figure 4:
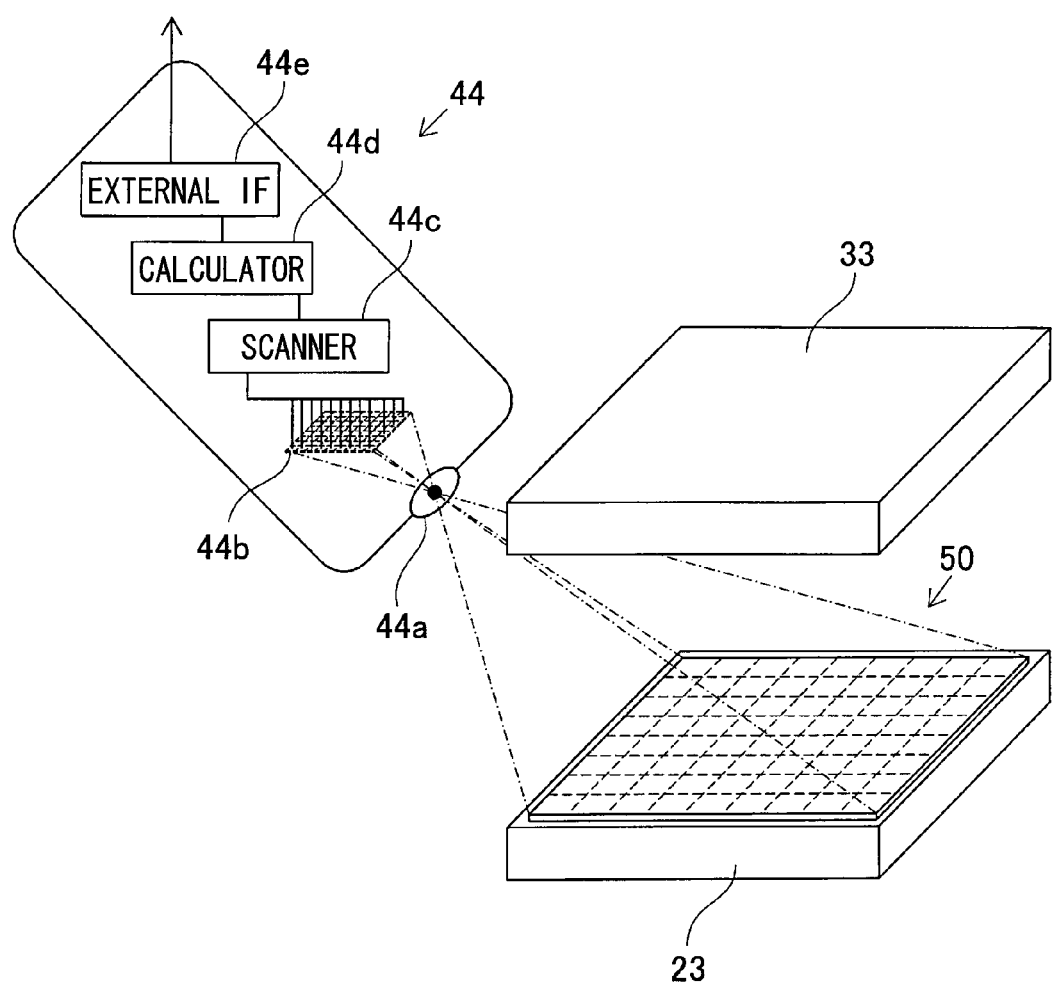
FIG. 4 is an explanatory drawing illustrating a temperature sensor of a foreign matter sensing device according to a second embodiment.
Figure 5:
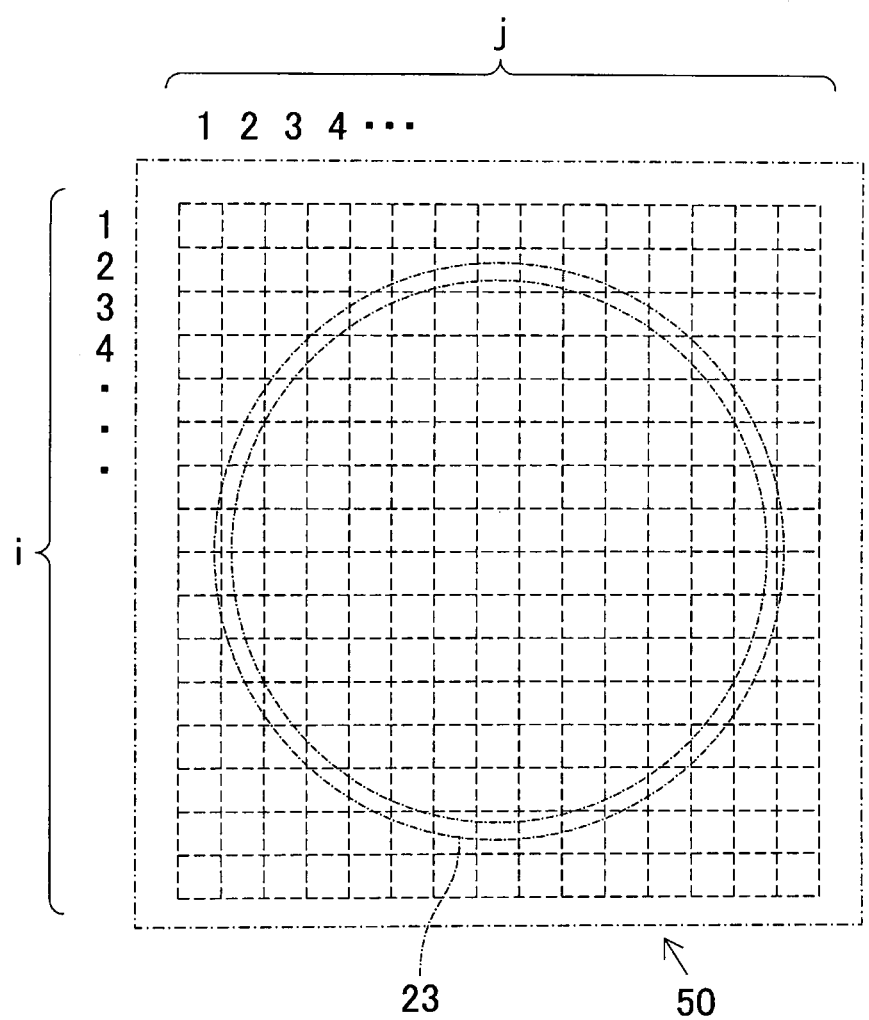
FIG. 5 is an explanatory drawing illustrating detection areas of a foreign matter detection range of the second embodiment.

A foreign matter sensing device and a non-contact electric-power transfer system according to a second embodiment are explained with reference to FIGS. 4 and 5. FIG. 4 is an explanatory drawing illustrating a temperature sensor 44 of the foreign matter sensing device 40 of the second embodiment. FIG. 5 is an explanatory drawing explaining the state where the foreign matter detection range 50 is divided into plural detection areas defined by a two-dimension identify number i and j.

The foreign matter sensing device 40 of the second embodiment includes the temperature sensor 44 instead of the temperature sensor 43 of the first embodiment, so as to raise the detection precision of exothermic foreign matter. The substantially same parts and the components as the first embodiment are indicated with the same reference numeral and the same description will not be reiterated.

The foreign matter sensing device 40 has the temperature sensor 44 which measures the temperature of the foreign matter detection range 50. The temperature sensor 44 is configured to detect the temperature for each detection area which is defined by dividing the foreign matter detection range 50 into plural detection areas. Specifically, as shown in FIG. 4, the temperature sensor 44 has a light-gathering lens 44a, a sensor unit 44b, a scanning part 44c, a calculator part 44d, and an external interface (IF) 44e.

The sensor unit 44b has plural pyroelectric elements. The light-gathering lens 44a is arranged so that each infrared light traveling from each detection area of the foreign matter detection range 50 enters the corresponding pyroelectric element of the plural pyroelectric elements of the sensor unit 44b. The scanning part 44c outputs a signal corresponding to the temperature for each detection area to the calculator part 44d by scanning each pyroelectric element. The temperature information of each detection area calculated by the calculator part 44d is outputted to the control part 41 through the external interface 44e.

That is, the temperature of each detection area of the foreign matter detection range 50 is measured with the temperature sensor 44, as shown in FIG. 5, as a measurement temperature Tij(t). When the foreign matter detection process is carried out by the control part 41, the measurement temperature Tij(t) is measured for each detection area by the temperature sensor 44 at S105. Then, each measurement temperature Tij(t) is determined to be lower than the temperature threshold Tth or not at S107.

Thus, the temperature is measured in each detection area of the foreign matter detection range 50, and the existence of foreign matter is determined at S107 based on the measurement temperature Tij(t) for each detection area. For example, the measurement temperature T(t) detected by the temperature sensor 43 does not become high even if the temperature is raised locally in the foreign matter detection range 50 because the heat of exothermic foreign matter is spread over the foreign matter detection range 50. In this case, the temperature sensor 44 can accurately detect the measurement temperature Tij(t) for the local detection area. That is, the temperature sensor 44 can provide the temperature of the foreign matter detection range 50 more in details, so the detection precision of exothermic foreign matter can be raised.

In order to reduce the processing load of the control part 41, the temperature may be measured in at least two detection areas of the foreign matter detection range 50, and the existence of foreign matter may be determined based on the measurement temperature for the at least two detection areas at S107. In this case, the temperature of the foreign matter detection range 50 is detected more details as compared with the case where the temperature sensor 43 is adopted, therefore the detection precision of exothermic foreign matter can be raised.

Figure 6:
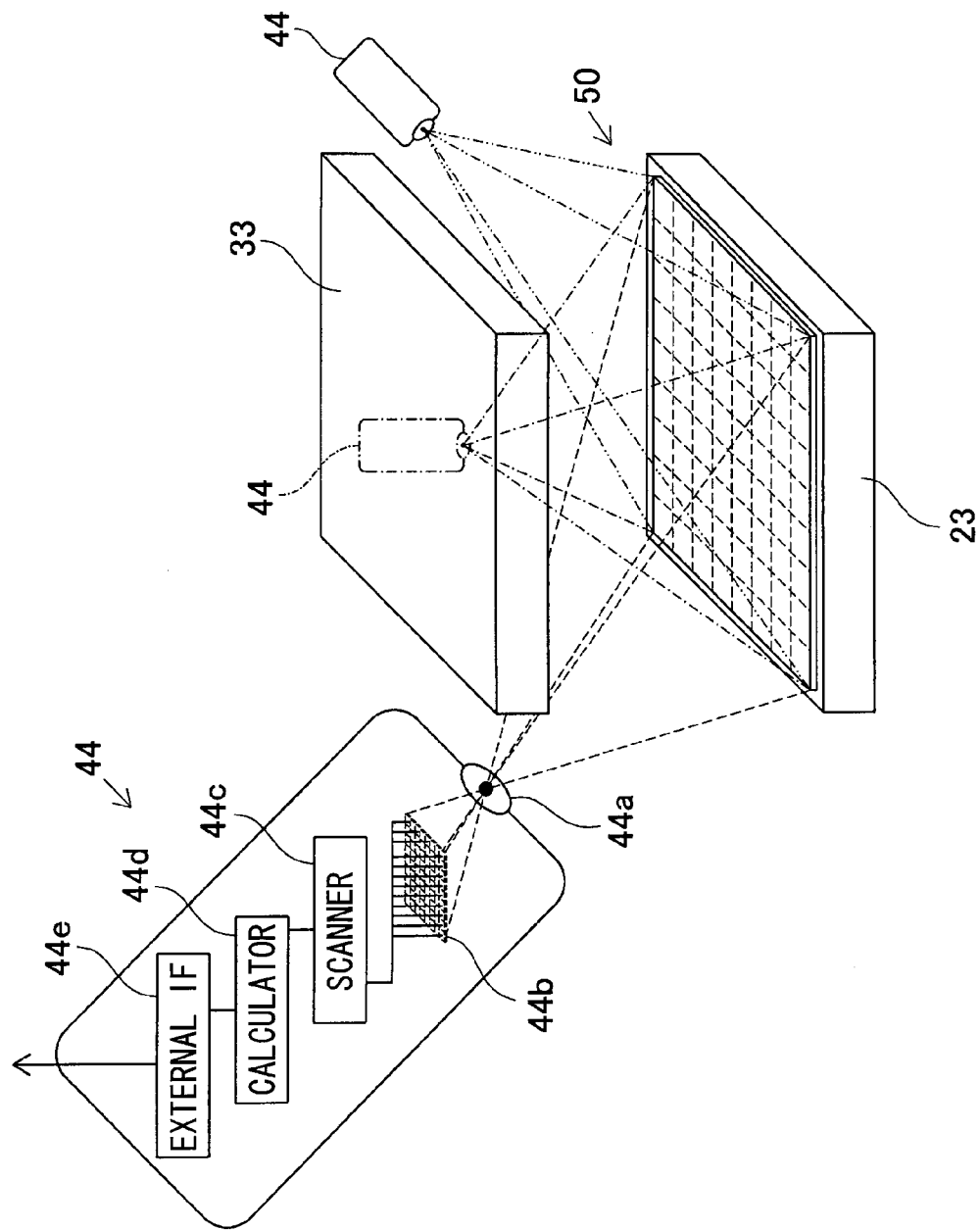
FIG. 6 is an explanatory drawing illustrating a first modification example of the second embodiment.

FIG. 6 is an explanatory drawing illustrating a first modification example of the second embodiment.

Figure 7A:
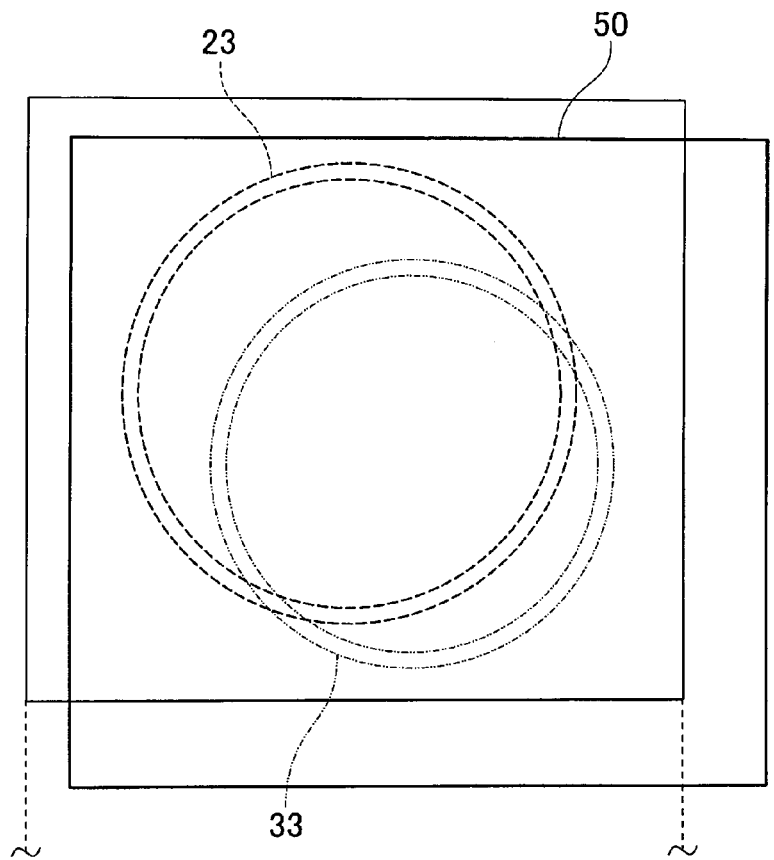
FIGS. 7A and 7B are explanatory drawings illustrating a second modification example of the second embodiment.
Figure 7B:
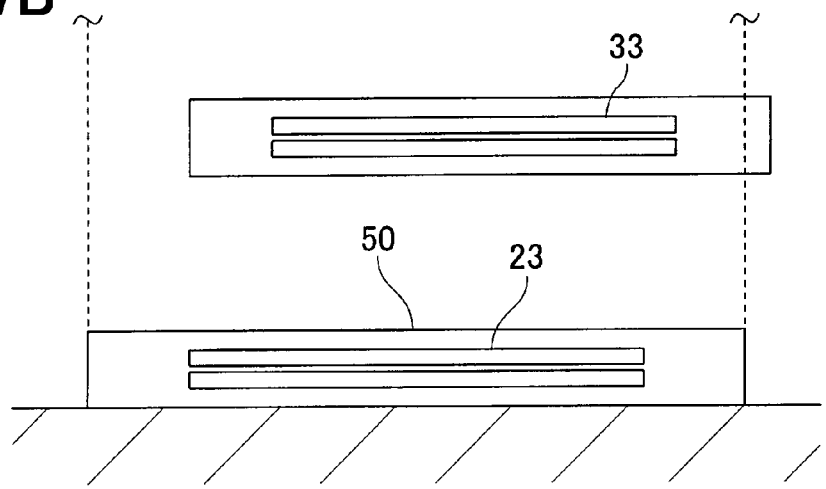

FIGS. 7A and 7B are explanatory drawings explaining the foreign matter detection range 50 according to a second modification example of the second embodiment. FIG. 7A illustrates the vehicle-side coil 33 projected on the foreign matter detection range 50, and FIG. 7B illustrates the position relationship between the coils 23, 33 along a road surface direction.

Figure 8A:
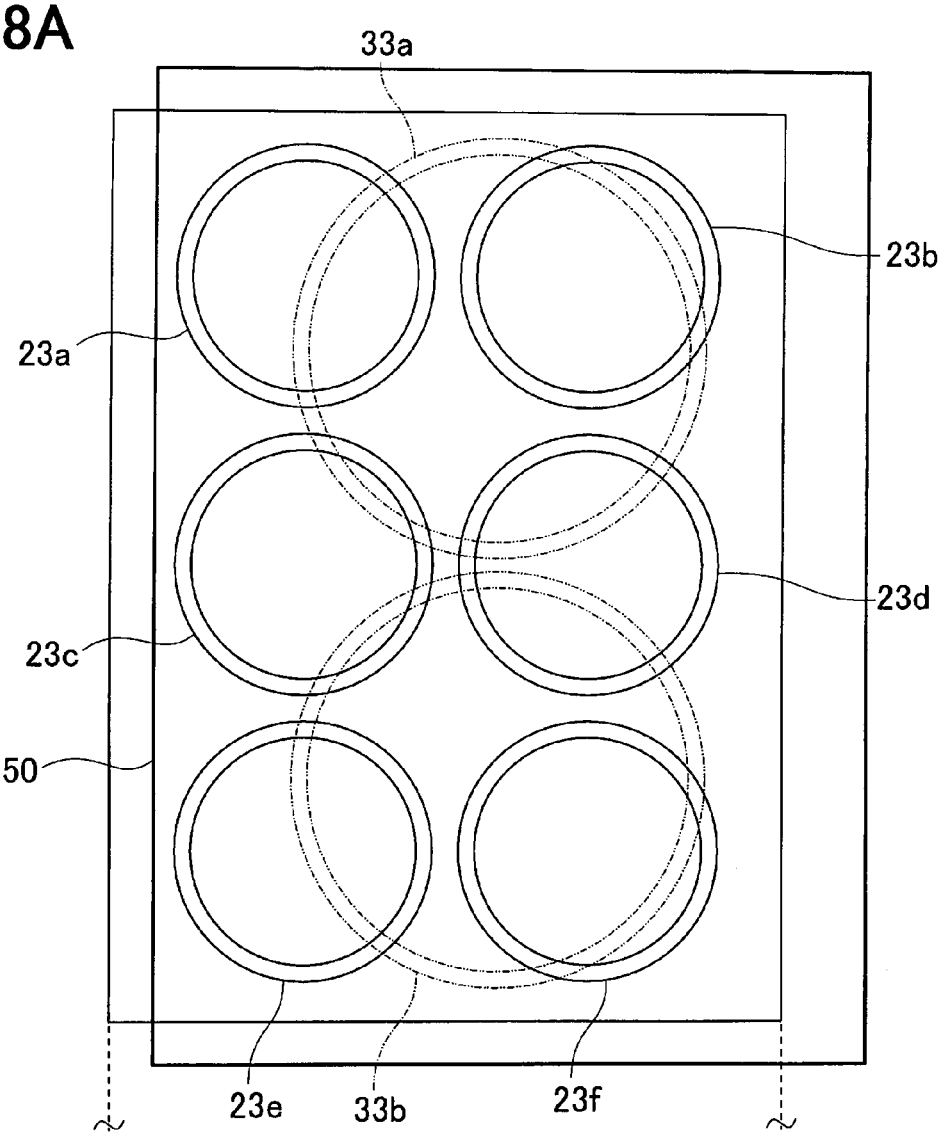
FIGS. 8A and 8B are explanatory drawings illustrating a third modification example of the second embodiment.
Figure 8B:
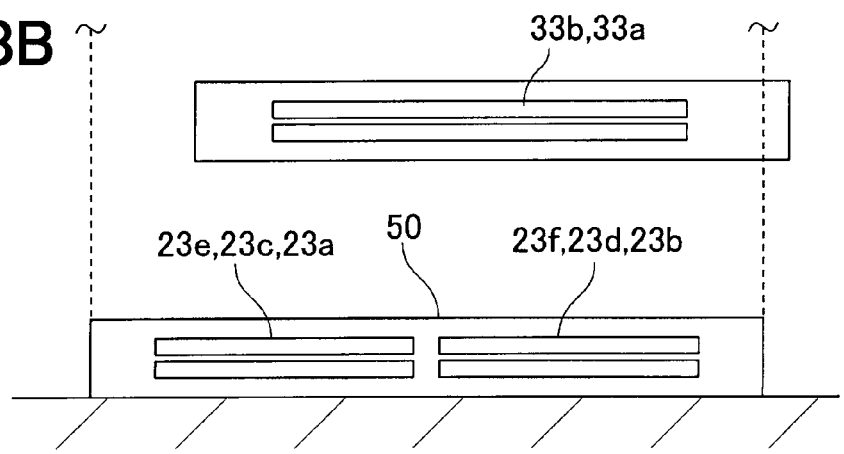

FIGS. 8A and 8B are explanatory drawings explaining the foreign matter detection range 50 according to a third modification example of the second embodiment. FIG. 8A illustrates the vehicle-side coil 33a, 33b projected on the foreign matter detection range 50, and FIG. 8B illustrates the position relationship between the coil 33a, 33b and the coil 23a, 23b, 23c, 23d, 23e, 23f along a road surface direction.

Figure 9A:
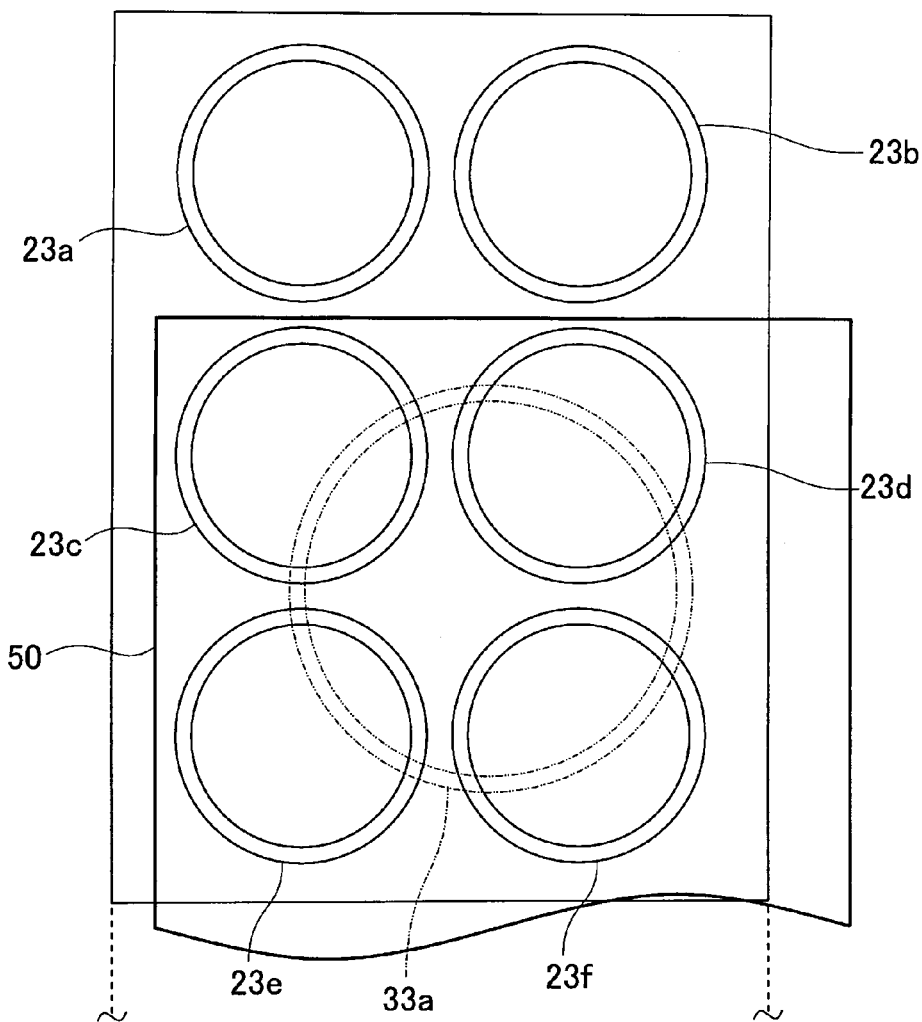
FIGS. 9A and 9B are explanatory drawings illustrating advantage of the third modification example of the second embodiment.
Figure 9B:
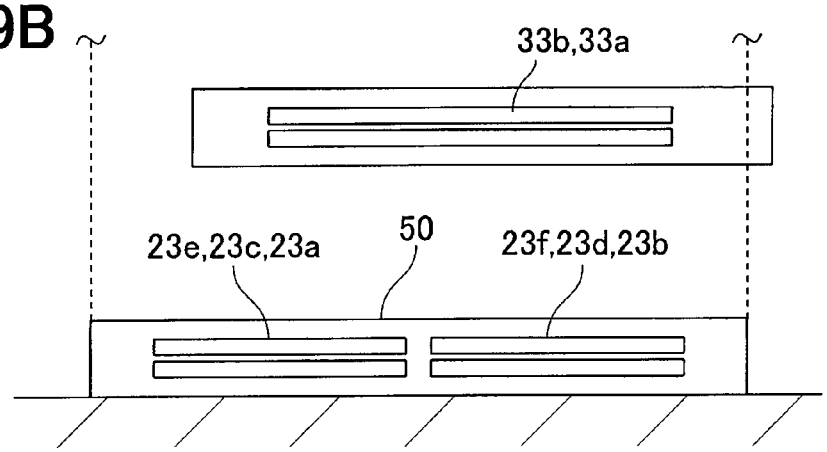

FIGS. 9A and 9B are explanatory drawings explaining the advantage of the third modification example of the second embodiment. FIG. 9A illustrates the vehicle-side coil 33a projected on the foreign matter detection range 50, and FIG. 9B illustrates the position relationship between the coil 33a, 33b and the coil 23a, 23b, 23c, 23d, 23e, 23f along a road surface direction.

Figure 10A:
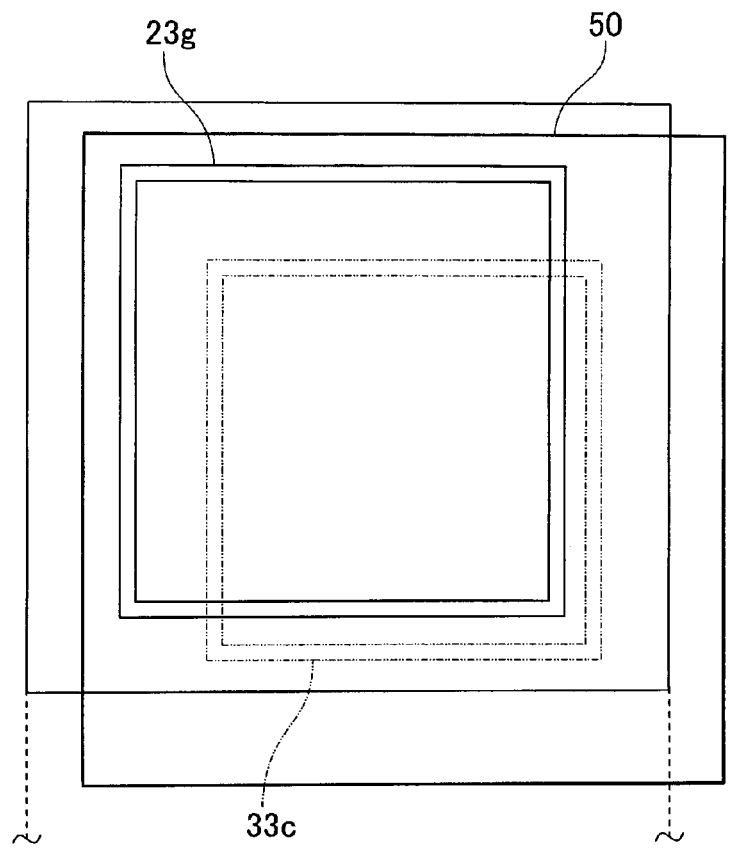
FIGS. 10A and 10B are explanatory drawings illustrating a fourth modification example of the second embodiment.
Figure 10B:
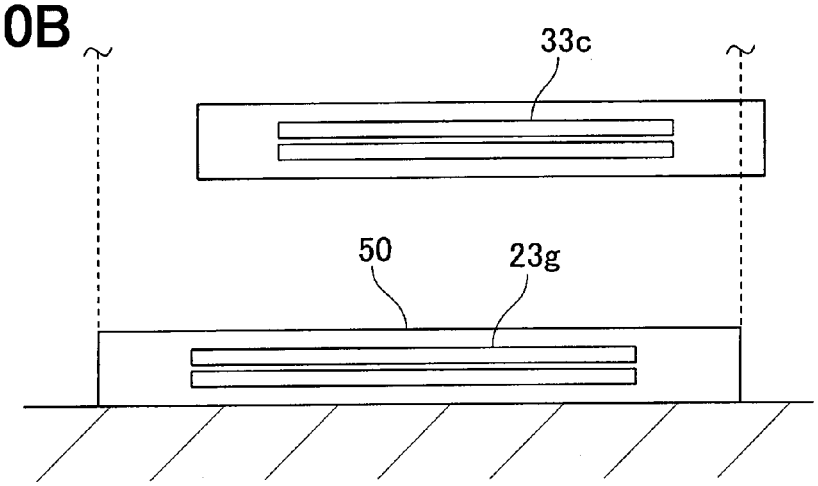

FIGS. 10A and 10B are explanatory drawings explaining the foreign matter detection range 50 according to a fourth modification example of the second embodiment. FIG. 10A illustrates the vehicle-side coil 33c projected on the foreign matter detection range 50, and FIG. 10B illustrates the position relationship between the coil 33c and the coil 23g along a road surface direction.

As shown in FIG. 6, as the first modification of the second embodiment, plural temperature sensors 44 are arranged around the vehicle-side coil 33 to detect the temperature in the detection areas. Because the temperature of the foreign matter detection range 50 is detected in plural directions broadly and in detail, even if there is an obstacle around the circumference of the foreign matter detection range 50, the detection precision of exothermic foreign matter can be raised more. In addition, one of the plural temperature sensors 44 is arranged to be located right above the out-of-vehicle coil 23. In this case, the influence of obstacle can become still smaller, so the detection precision of exothermic foreign matter can be raised more.

The second modification example of the second embodiment will be described with reference to FIGS. 7A and 7B. If the vehicle 30 is located to deviate from a regular position when the vehicle 30 is parked at the parking space, a position gap may be generated in the road surface direction between the vehicle-side coil 33 and the out-of-vehicle coil 23. The temperature sensor 43 and the camera 42 are arranged around the vehicle-side coil 33. If the coils 33 and 23 have the position gap with each other as mentioned above, a part of the area defined by projecting the out-of-vehicle coil 23 to the foreign matter detection range 50 may be deviated from the foreign matter detection range 50. In this case, it becomes difficult to raise the detection precision of exothermic foreign matter even when the temperature is measured in the detection areas.

Then, as the second modification of the second embodiment shown in FIGS. 7A and 7B, in consideration of the above position gap, the foreign matter detection range 50 is set larger than the range defined by projecting the vehicle-side coil 33 on the road surface. Therefore, in the case where the vehicle 30 is parked to have the non-contact electric-power transfer, even if a position gap is generated in the road surface direction between the vehicle-side coil 33 and the out-of-vehicle coil 23, an exothermic foreign matter can be made easy to detect.

The third modification example of the second embodiment will be described with reference to FIGS. 8A, 8B, 9A and 9B. The vehicle-side coil is made of plural coils, for example, is made of two coils 33a and 33b, as shown in FIG. 8A. Moreover, the out-of-vehicle coil is made of plural coils, for example, is made of six coils 23a, 23b, 23c, 23d, 23e, 23f (referred as 23a-23f) in FIG. 8A.

In this case, the foreign matter detection range 50 is set to include all the out-of-vehicle coil 23a-23f that carries out the non-contact electric-power transfer with the vehicle-side coil 33a, 33b. Therefore, when the vehicle 30 is parked to have non-contact electric-power transfer, even if a position gap is generated in the road surface direction between the vehicle-side coil and the out-of-vehicle coil, an exothermic foreign matter can be made easy to detect, similarly to the second modification example of the second embodiment.

Moreover, because the position gap is generated in the road surface direction between the vehicle-side coil and the out-of-vehicle coil, as shown in FIGS. 9A and 9B, when non-contact electric-power transfer is carried out between the vehicle-side coil 33a and the out-of-vehicle coils 23c, 23d, 23e, 23f, the foreign matter detection range 50 will be set to include the out-of-vehicle coils 23c, 23d, 23e, 23f except for the out-of-vehicle coils 23a and 23b.

Thus, when the foreign matter detection range 50 is set to include the out-of-vehicle coils performing the non-contact electric-power transfer, unnecessary foreign matter detection area can be eliminated compared with the case where a foreign matter detection range is set to include all the out-of-vehicle coils. Therefore, not only the detection precision of exothermic foreign matter is raised, but also the processing load relating to the detection of exothermic foreign matter is reduced.

Moreover, as the fourth modification example of the second embodiment, as shown in FIGS. 10A and 10B, the vehicle-side coil 33c and the out-of-vehicle coil 23g may be formed in a rectangular shape, for example, instead of the circle shape.

In addition, the second embodiment and the modification examples of the second embodiment may be applied to other embodiment.

(Third Embodiment)

Figure 11:
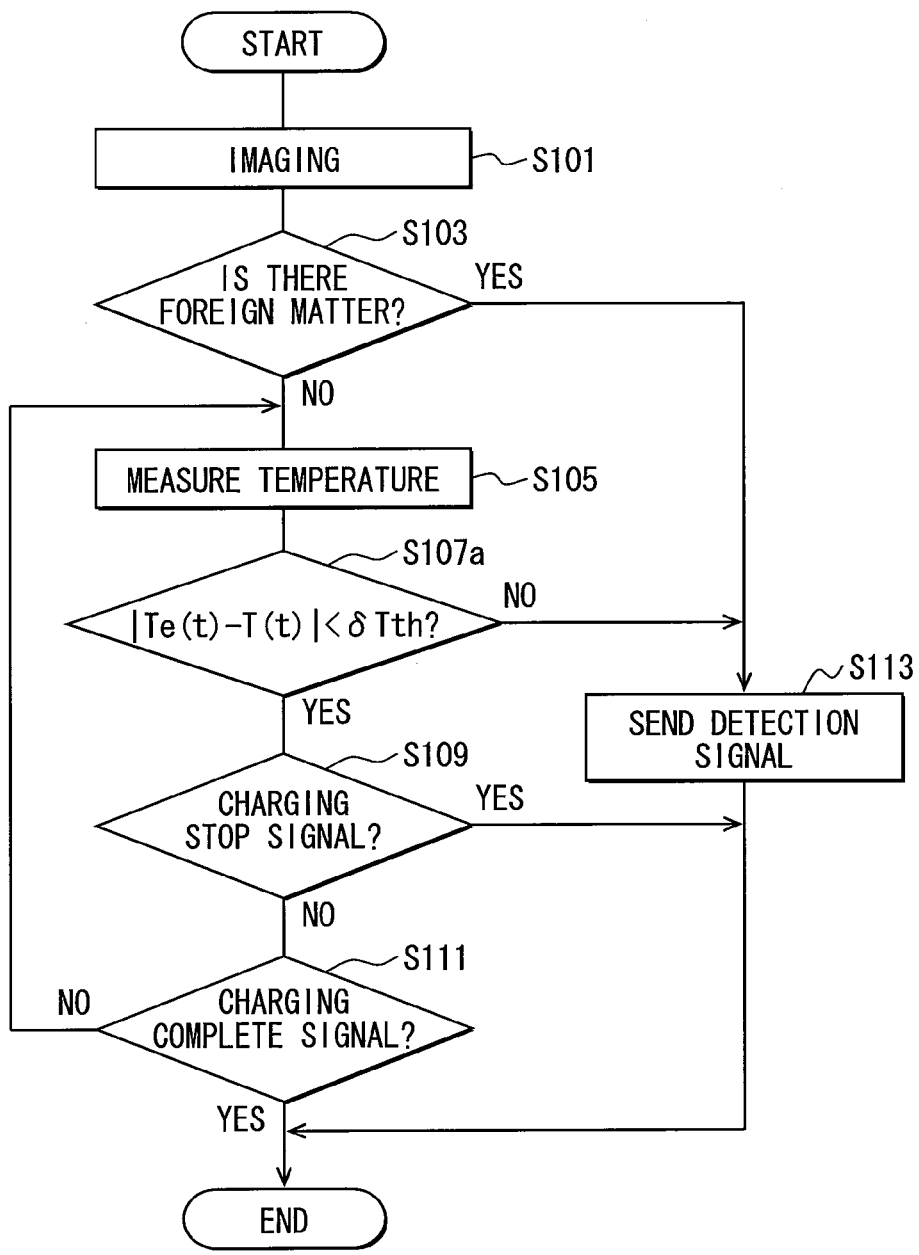
FIG. 11 is a flow chart illustrating a foreign matter detection process according to a third embodiment.
Figure 12:
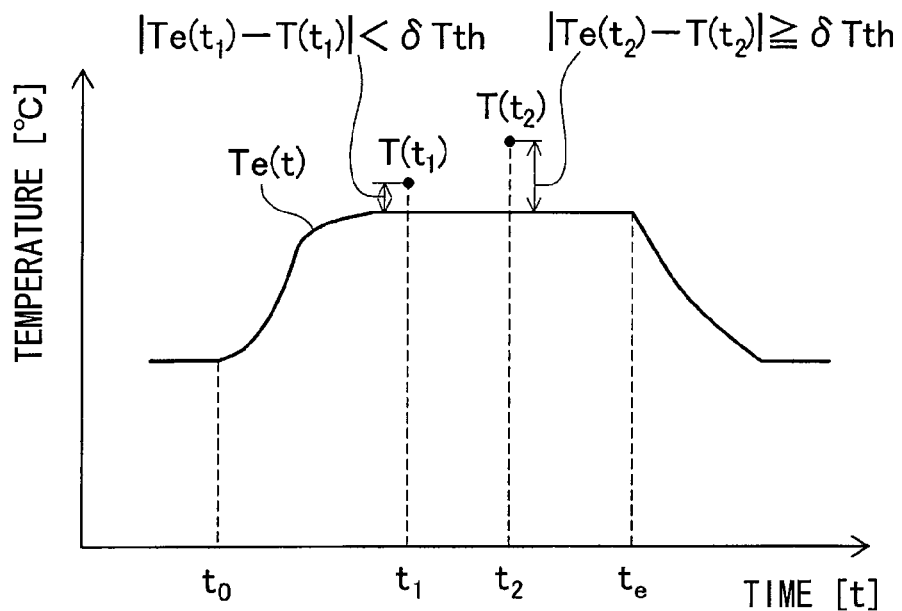
FIG. 12 is a graph illustrating a relationship between a measurement temperature and a prediction temperature of the third embodiment.

A foreign matter sensing device and a non-contact electric-power transfer system concerning a third embodiment are explained with reference to FIGS. 11 and 12. FIG. 11 is a flow chart illustrating a foreign matter detection process of the third embodiment. FIG. 12 is an explanatory drawing illustrating the relationship between the measurement temperature T(t) and the prediction temperature Te(t) in the third embodiment.

The foreign matter sensing device 40 of the third embodiment executes the foreign matter detection process based on the flow chart of FIG. 11 instead of the flow chart of FIG. 3 of the first embodiment, in order to raise the detection precision of exothermic foreign matter. The substantially same parts and components as the first embodiment are indicated with the same reference numeral and the same description will not be reiterated.

In the third embodiment, the prediction temperature Te(t) is set in advance, as shown in FIG. 12, with an assumption that there is no exothermic foreign matter in the foreign matter detection range 50. The prediction temperature Te(t) of the foreign matter detection range 50 is changed with elapsed-time due to the non-contact electric-power transfer. In FIG. 12, the timing $t_o$ represents a start time of the non-contact electric-power transfer, and the timing $t_e$ represents a finish time of the non-contact electric-power transfer.

As shown in FIG. 12, the temperature of the foreign matter detection range 50 is comparatively low at the start time of the non-contact electric-power transfer, and is raised by heat generated by the out-of-vehicle coil 23 when the non-contact electric-power transfer is continued. Then, the measurement temperature T(t) measured by the temperature sensor 43 is compared with the prediction temperature Te(t) set in consideration of heat generated by the out-of-vehicle coil 23, thereby the detection precision of exothermic foreign matter can be raised. In addition, information about the prediction temperature Te(t) is beforehand memorized in the memory of the control part 41.

As shown in the flow chart of FIG. 11, specifically, the absolute value of the subtraction between the measurement temperature T(t) measured at S105 and the prediction temperature Te(t) is determined to be smaller than a predetermined threshold value δTth or not at S107a. The predetermined threshold value δTth is a constant value which does not change according to time, and is set on the assumption that a foreign matter such as metal piece exists in the foreign matter detection range 50 and that the foreign matter generates heat according to the non-contact electric-power transfer between the coils 23 and 33. In addition, the predetermined threshold value δTth may be changed according to the time progress from the start timing of non-contact electric-power transfer.

For example, at the timing $t_1$ in FIG. 12, the absolute value of the subtraction between the measurement temperature $T(t_1)$ and the prediction temperature $Te(t_1)$ is smaller than the predetermined threshold value δTth (Yes at S107a), the non-contact electric-power transfer will be continued, without outputting a foreign matter detection signal.

On the other hand, at the timing $t_2$ in FIG. 12, the absolute value of the subtraction between the measurement temperature $T(t_2)$ and the prediction temperature $Te(t_2)$ is larger than or equal to the predetermined threshold value δTth (No at S107a), so a foreign matter detection signal is outputted at S113 to inform that an exothermic foreign matter emits heat in the foreign matter detection range 50.

Thus, the existence of the foreign matter in the foreign matter detection range 50 is determined according to the comparison between the prediction temperature Te(t) and the measurement temperature T(t). When the measurement temperature T(t) exceeds the prediction temperature Te(t) by the assumed value, it is presumed that an exothermic foreign matter emits heat in the foreign matter detection range 50. Therefore, the detection precision of exothermic foreign matter can be raised by setting the prediction temperature according to ambient environment.

Figure 14:
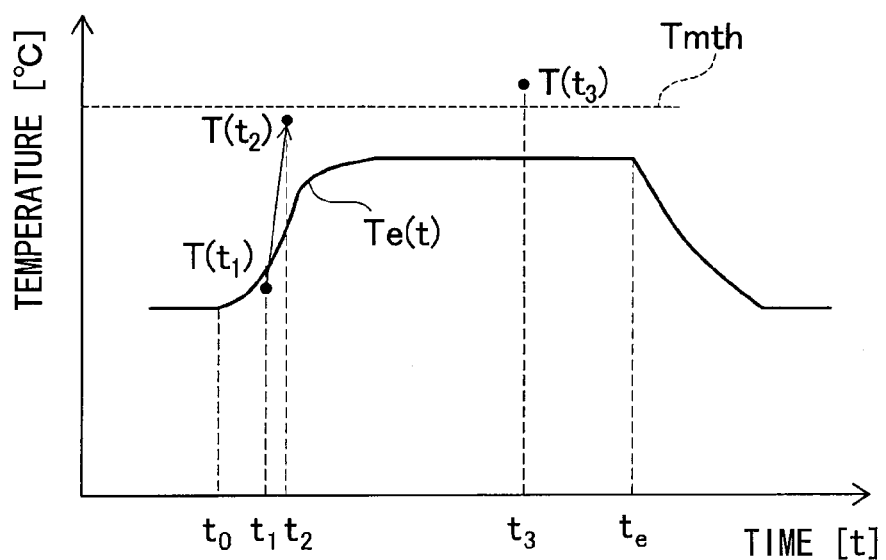
FIG. 14 is a graph illustrating a relationship between a measurement temperature and a prediction temperature of the modification example of the third embodiment.
Figure 13:
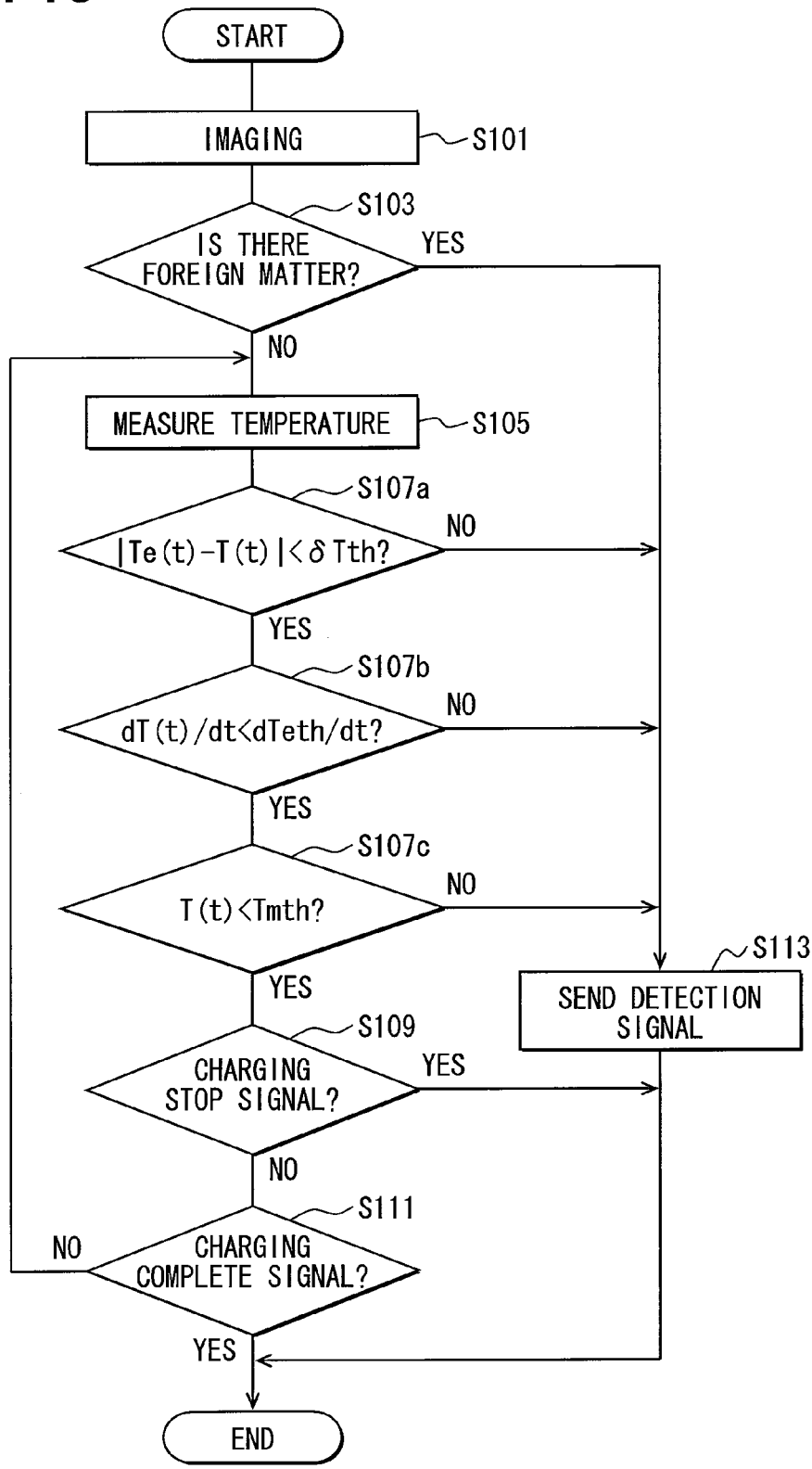
FIG. 13 is a flow chart illustrating a modification example of the third embodiment.

FIG. 13 is a flow chart illustrating a modification example of the third embodiment. FIG. 14 is an explanatory drawing illustrating the relationship between the measurement temperature and the prediction temperature in the modification example of the third embodiment.

As the modification example of the third embodiment, as shown in S107b of FIG. 13, when a temperature variation amount dT(t)/dt of the measurement temperature T(t) is larger than or equal to a variation threshold dTeth/dt (No at S107b) which is set to assume that heat is generated by a foreign matter, a foreign matter detection signal is outputted to inform that the foreign matter is emitting heat in the foreign matter detection range 50.

For example, as shown in FIG. 14, the measurement temperature T(t) is suddenly raised from $T(t_1)$ at the timing $t_1$ to $T(t_2)$ at the timing $t_2$. At this time, the temperature variation amount dT(t)/dt becomes more than the variation threshold dTeth/dt (No at S107b), so a foreign matter detection signal is outputted. Thus, the foreign matter can be quickly detected.

Moreover, as shown in S107c of FIG. 13, when the measurement temperature T(t) is more than an upper limit threshold Tmth set to assume that heat is generated by a foreign matter (No at S107c), a foreign matter detection signal is output to inform that the foreign matter is emitting heat in the foreign matter detection range 50.

For example, as shown in FIG. 14, when the measurement temperature $T(t_3)$ becomes larger than the upper limit threshold Tmth at the timing $t_3$ (No at S107c), a foreign matter detection signal is outputted. Thus, the foreign matter can be surely detected.

The third embodiment and the modification example of the third embodiment may be applied to other embodiment.

(Fourth Embodiment)

Figure 15:
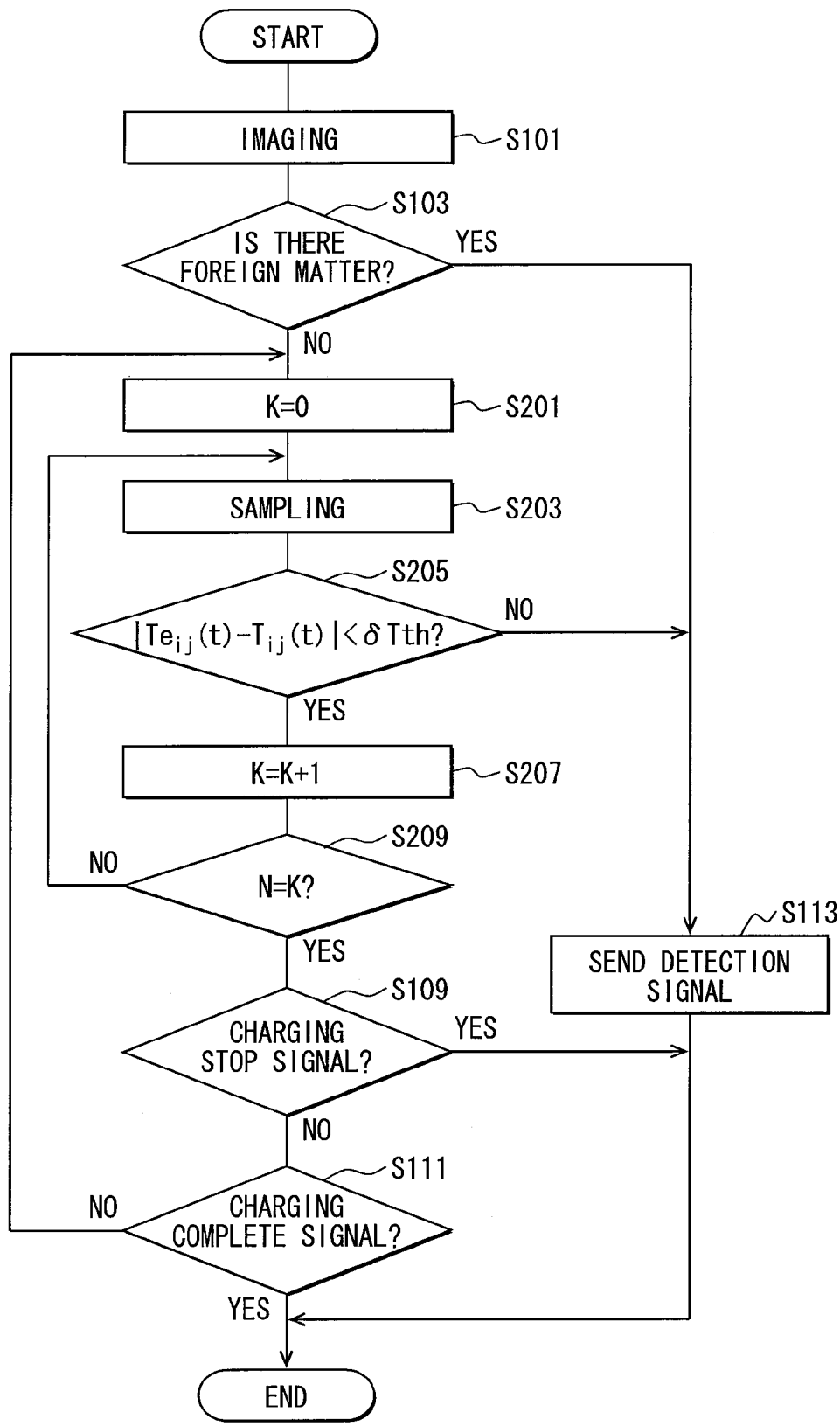
FIG. 15 is a flow chart illustrating a foreign matter detection process according to a fourth embodiment.

A foreign matter sensing device and a non-contact electric-power transfer system concerning a fourth embodiment are explained with reference to FIG. 15. FIG. 15 is a flow chart illustrating a foreign matter detection process of the fourth embodiment.

The foreign matter sensing device 40 of the fourth embodiment executes the foreign matter detection process based on the flow chart of FIG. 15 instead of the flow chart of FIG. 3, in order to raise the detection precision of exothermic foreign matter. The substantially same parts and components as the second embodiment are indicated with the same reference numeral and the same description will not be reiterated.

In the fourth embodiment, the prediction temperature of the third embodiment is beforehand set for each detection area as $Te_{ij}(t)$. N of detection areas are sampled at random from all the detection areas, and N of the measurement temperatures $T_{ij}(t)$ measured with the temperature sensor 44 are compared with the prediction temperature $Te_{ij}(t)$. Thus, the detection precision of exothermic foreign matter is raised.

The foreign matter detection process in this embodiment is explained using the flow chart shown in FIG. 15.

When a foreign matter is not imaged in the image taken at S101 (No at S103), K is set as 0 (K=0) at S201. K is equivalent to the number of the detection areas through which the measurement temperature $T_{ij}(t)$ and the prediction temperature $Te_{ij}(t)$ are compared with each other. Next, an individual temperature sampling is conducted at S203, therefore one measurement temperature $T_{ij}(t)$ is extracted at random from the plural measurement temperatures $T_{ij}(t)$.

Then, at S205, the absolute value of the subtraction between the extracted measurement temperature $T_{ij}(t)$ and the prediction temperature $Te_{ij}(t)$ is determined to be less than the predetermined threshold δTth or not. When the absolute value of the subtraction between the extracted measurement temperature $T_{ij}(t)$ and the prediction temperature $Te_{ij}(t)$ is less than the predetermined threshold δTth (Yes at S205), K is incremented by one (K=K+1) at S207. When the incremented K=K+1 is less than N which is the number of the detection areas (No at S209), the process is returned to S203. That is, the absolute value of the subtraction between the measurement temperature $T_{ij}(t)$ and the prediction temperature $Te_{ij}(t)$ is compared with the predetermined threshold δTth in the N of the detection areas.

When the absolute value of the subtraction between the measurement temperature $T_{ij}(t)$ and the prediction temperature $Te_{ij}(t)$ is less than the predetermined threshold δTth in all the N of the detection areas, K becomes equal to N (Yes at S209).

When both the charging stop signal and the charging complete signal are not received (No at S109 and S111), K is set as 0 (K=0) at S201, then the process is continued from S203 again. Thus, the measurement temperature $T_{ij}(t)$ and the prediction temperature $Te_{ij}(t)$ are compared with each other in N of the detection areas which are extracted at random.

Thus, the existence of foreign matter is determined by comparing the measurement temperature $T_{ij}(t)$ and the prediction temperature $Te_{ij}(t)$ in N of the detection areas which are extracted at random. Therefore, the temperature of the foreign matter detection range 50 can be detected more in details, and the detection precision of exothermic foreign matter can be raised more by setting the prediction temperature according to ambient environment.

(Fifth Embodiment)

A foreign matter sensing device and a non-contact electric-power transfer system concerning a fifth embodiment are explained with reference to FIGS. 16-21.

FIG. 16 is a block diagram illustrating a foreign matter sensing device 40a and a non-contact electric-power transfer system 10a of the fifth embodiment.

Figure 17A:
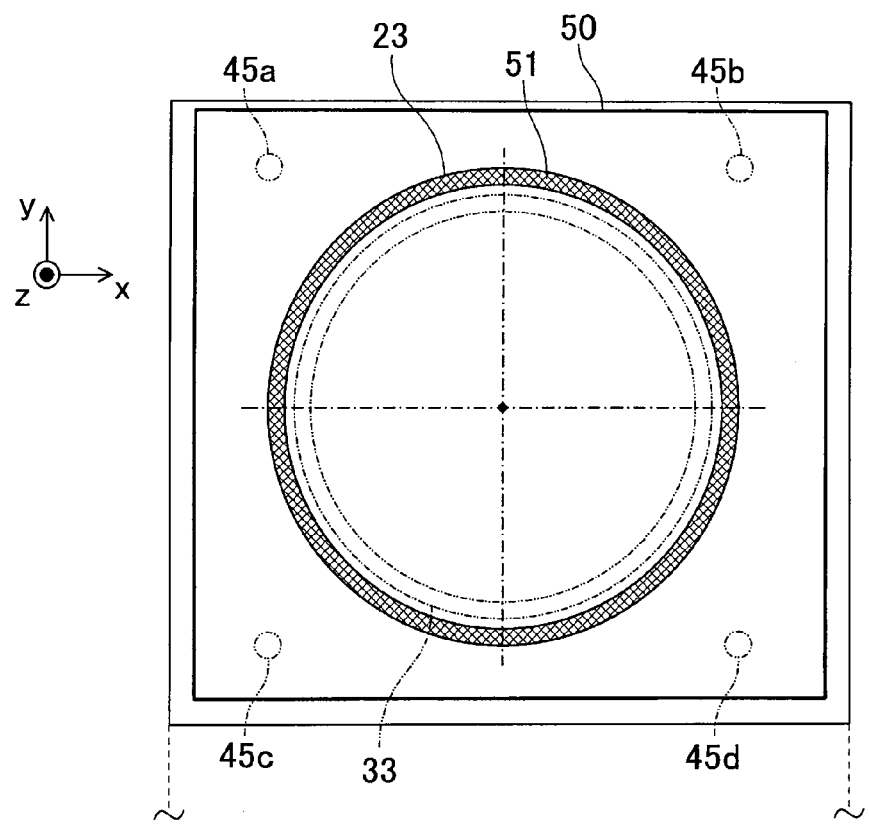
FIGS. 17A and 17B are explanatory drawings explaining a reference position of a vehicle-side coil relative to an out-of-vehicle coil of the fifth embodiment.
Figure 17B:
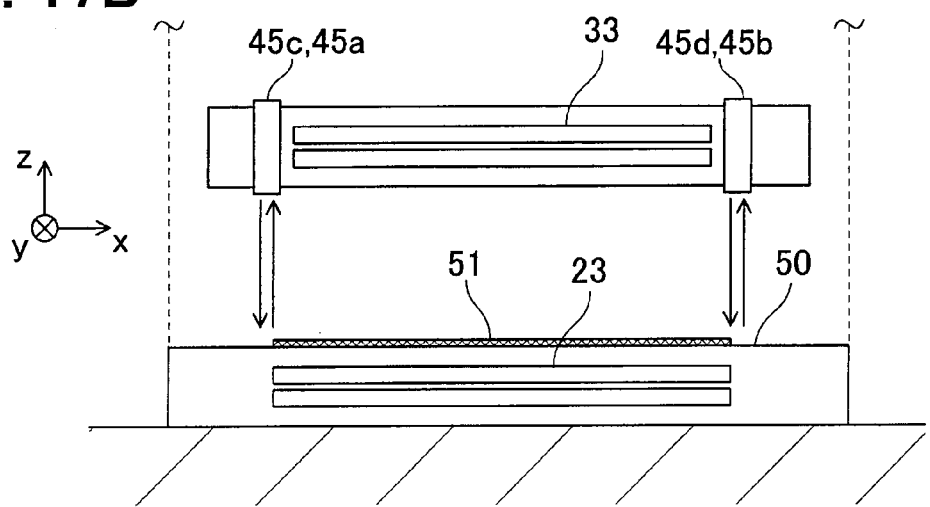

FIGS. 17A and 17B are explanatory drawings illustrating the vehicle-side coil 33 located at a reference position relative to the out-of-vehicle coil 23. FIG. 17A illustrates the vehicle-side coil 33 projected on the foreign matter detection range 50, and FIG. 17B illustrates the position relationship between the coils 23, 33 along a road surface direction.

Figure 18A:
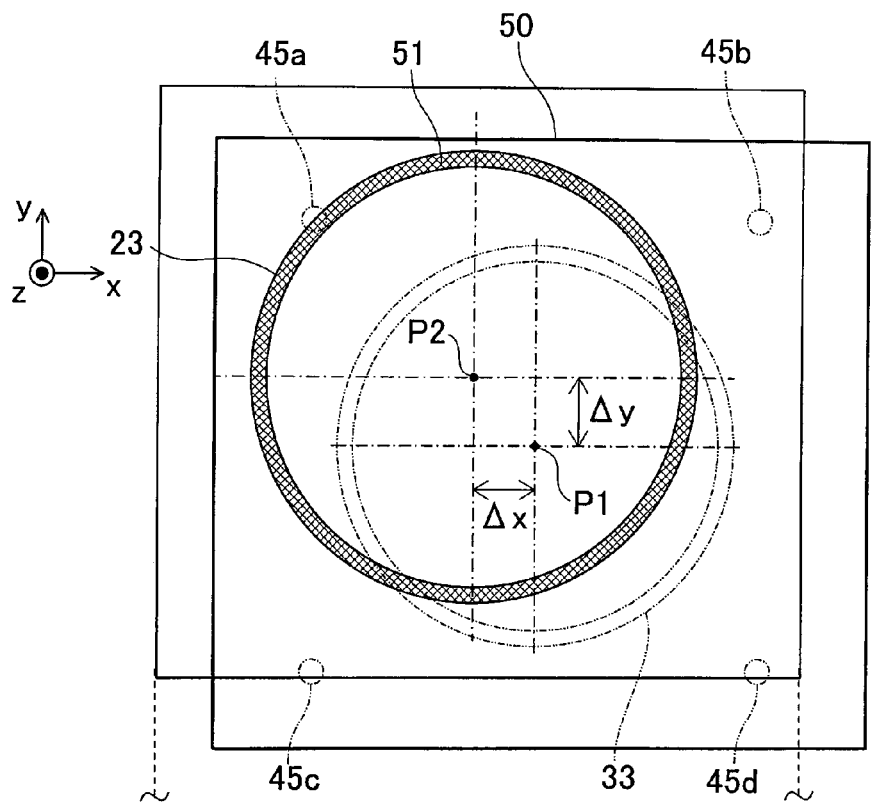
FIGS. 18A and 18B are explanatory drawings in which the vehicle-side coil has a position displacement and inclination relative to the out-of-vehicle coil.
Figure 18B:
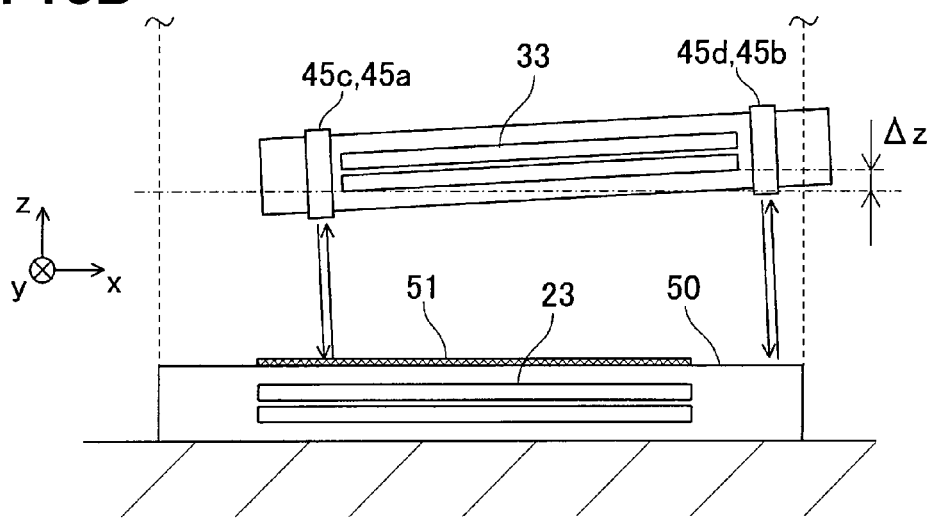

FIGS. 18A and 18B are explanatory drawings illustrating the vehicle-side coil 33 having a position displacement and inclination relative to the out-of-vehicle coil 23. FIG. 18A illustrates the vehicle-side coil 33 projected on the foreign matter detection range 50, and FIG. 18B illustrates the position relationship between the coils 23, 33 along a road surface direction.

Figure 19:
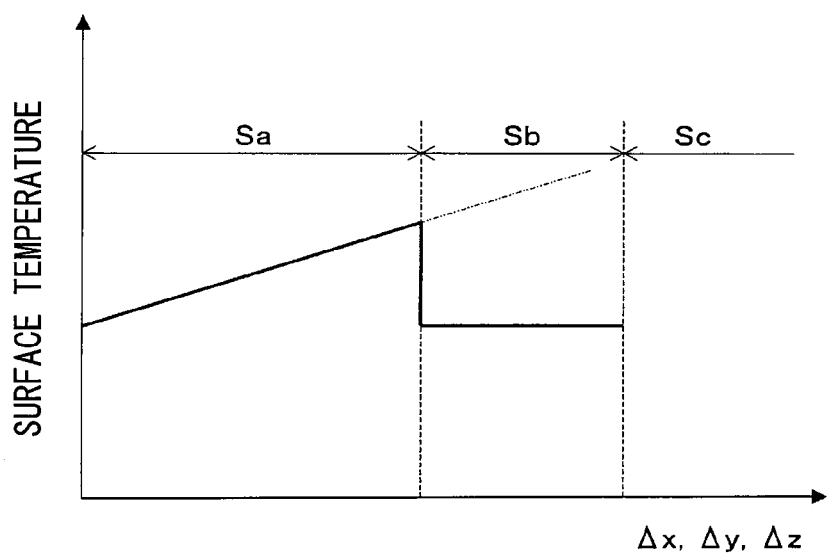
FIG. 19 is a graph illustrating a relationship between the position displacement and inclination and a surface temperature of the out-of-vehicle coil.
Figure 21:
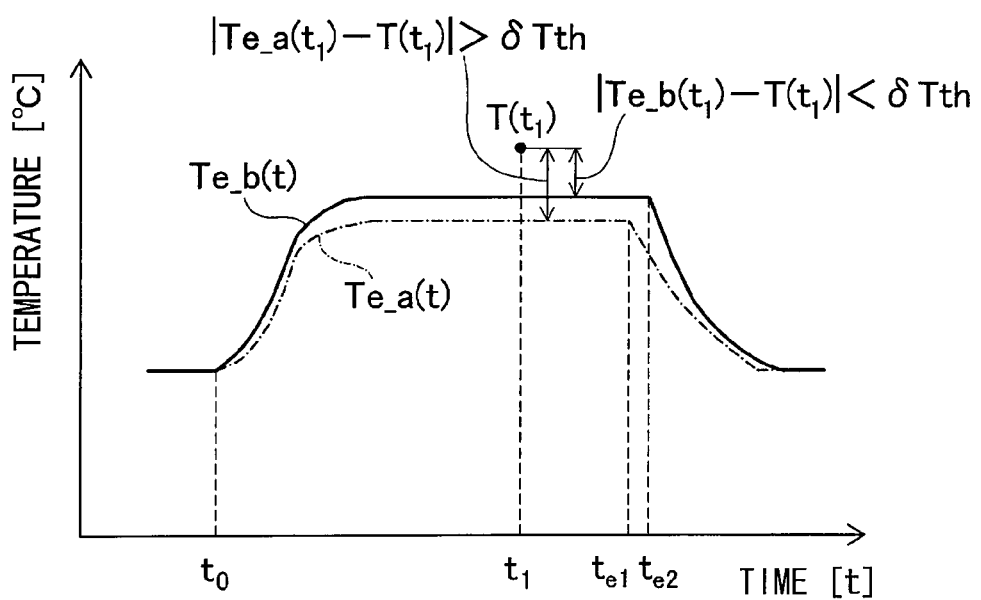
FIG. 21 is a graph illustrating a relationship between a basis prediction temperature and a corrected prediction temperature of the fifth embodiment.
Figure 20:
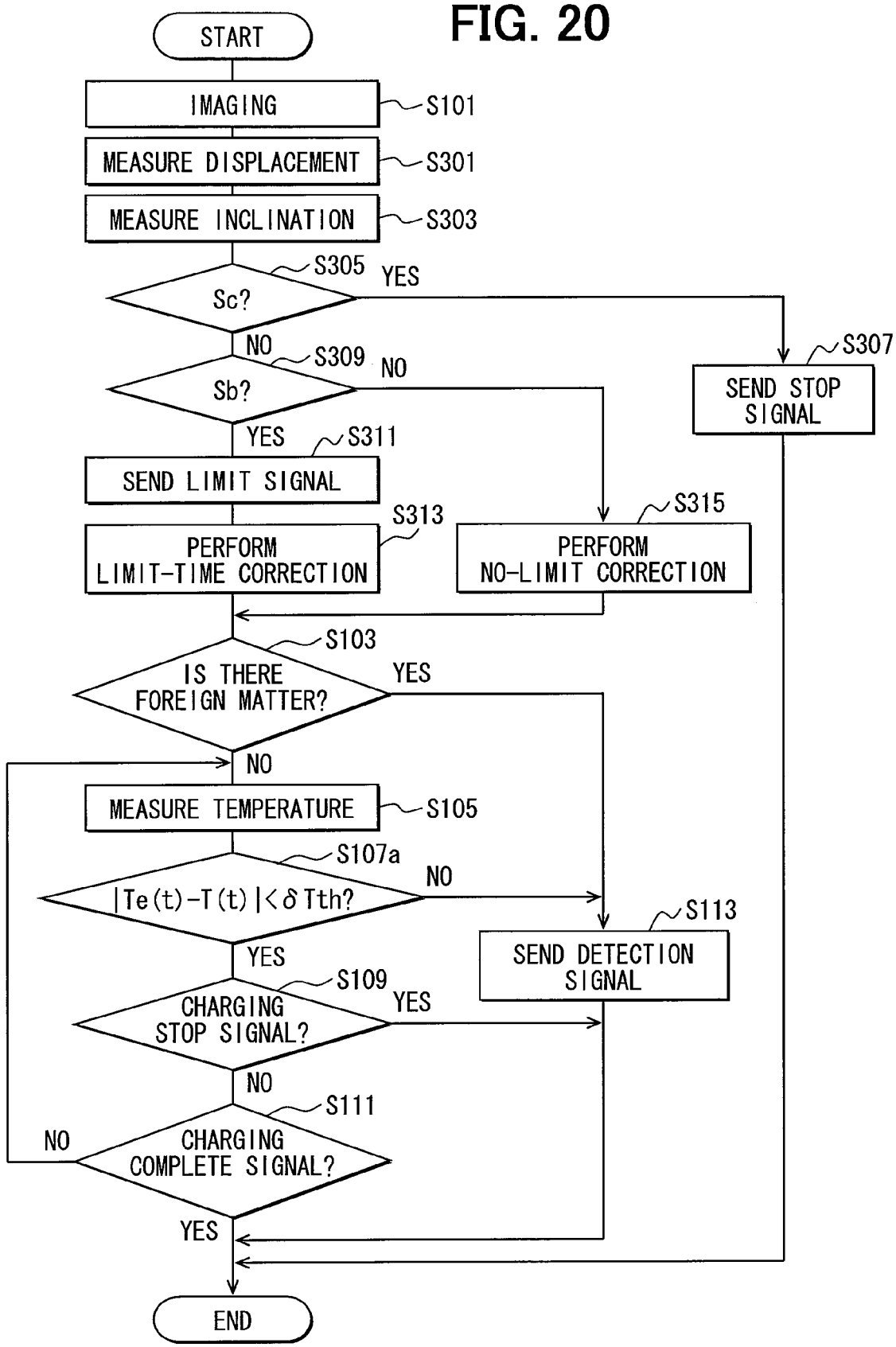
FIG. 20 is a flow chart illustrating a foreign matter detection process of the fifth embodiment.

FIG. 19 is a graph illustrating the relationship between the position displacement and inclination and the surface temperature of the out-of-vehicle coil 23. FIG. 20 is a flow chart illustrating a foreign matter detection process of the fifth embodiment. FIG. 21 is an explanatory drawing illustrating the relationship between a basis prediction temperature Te_a(t) and an after-correction prediction temperature Te_b(t) in the fifth embodiment.

The foreign matter sensing device 40a of the fifth embodiment corrects the prediction temperature Te(t) according to the amount of position displacement and inclination between the vehicle-side coil 33 and the out-of-vehicle coil 23, in order to raise the detection precision of exothermic foreign matter. The foreign matter sensing device 40a further includes ultrasonic sensors 45a-45d for measuring the inclination. The foreign matter detection process of the fifth embodiment is carried out based on the flow chart of FIG. 20 instead of FIG. 11 of the third embodiment. The substantially same parts and components as the third embodiment are indicated with the same reference numeral and the same description will not be reiterated.

As shown in FIG. 16, the foreign matter sensing device 40a of the non-contact electric-power transfer system 10a further has four ultrasonic sensors 45a, 45b, 45c, 45d (referred as 45a-45d), compared with the foreign matter sensing device 40. As shown in FIG. 17A, the ultrasonic sensors 45a-45d are arranged at equal intervals near the circumference of the vehicle-side coil 33, and oppose the foreign matter detection range 50. The ultrasonic sensors 45a-45d measure the distance to the foreign matter detection range 50 according to the time lag from a sending of ultrasonic wave to a receiving of the ultrasonic wave reflected by the foreign matter detection range 50. Each of the ultrasonic sensors 45a-45d is constructed to output the distance signal according to the measurement distance to the control part 41.

Moreover, as shown in FIG. 17A, a luminescent luminous paint 51 is applied to a portion of the foreign matter detection range 50 overlapping with the out-of-vehicle coil 23 as a positional information indicating part to calculate a relative position of the foreign matter detection range 50 with respect to the out-of-vehicle coil 23. The luminous paint 51 is represented by a hatching area of FIG. 17A.

In the foreign matter detection process of the present embodiment, a basis prediction temperature Te_a(t) is set to include no position gap and no inclination, and is corrected into an after-correction prediction temperature Te_b(t) according to the position gap or inclination between the vehicle-side coil 33 and the out-of-vehicle coil 23. The reason for correcting the prediction temperature Te(t) according to the position gap or inclination between the coils 33 and 23 is explained below with reference to FIGS. 17A-19.

As shown in FIGS. 17A and 17B, when the vehicle-side coil 33 is located to be parallel with the road surface and to have the center position agreeing with the center position of the out-of-vehicle coil 23 (that is, when the vehicle-side coil 33 is located at a reference position), the power transmission efficiency of the non-contact electric-power transfer between the coils 33 and 23 becomes the maximum.

However, as shown in FIGS. 18A and 18B, when the center P1 of the vehicle-side coil 33 is displaced from the center P2 of the out-of-vehicle coil 23 along the road surface direction by a displacement dimension of Δx and Δy, or when the vehicle-side coil 33 inclines to the out-of-vehicle coil 23 by an inclination of Δz, the power transmission efficiency will be lowered according to such a position gap and inclination. In this case, because generation of heat by the out-of-vehicle coil 23 will be increased compared with the case where the vehicle-side coil 33 is located at the reference position (refer to FIGS. 17A and 17B). Therefore, the prediction temperature Te(t) may become relatively low, and an exothermic foreign matter may be incorrectly detected.

As shown in FIG. 19, the charging current is not restricted in a normal range Sa where the displacement dimension of Δx and Δy and the inclination of Δz are comparatively small, and the surface temperature of the out-of-vehicle coil 23 is raised according to the displacement dimension of Δx and Δy and the inclination of Δz.

In an electric current restriction range Sb where the displacement dimension of Δx and Δy and the inclination of Δz are comparatively large, the charging current is restricted. In the electric current restriction range Sb, while the displacement dimension of Δx and Δy and the inclination of Δz are permissible, it is required to limit the generation of heat which is caused by deterioration in the charging efficiency, so the surface temperature of the out-of-vehicle coil 23 is maintained at the steady value.

In an electric-power transfer stop range Sc where the displacement dimension of Δx and Δy and the inclination of Δz exceed the electric current restriction range Sb, the non-contact electric-power transfer between the coils 33 and 23 is stopped.

The foreign matter detection process is explained with reference to the flow chart shown in FIG. 20.

After the foreign matter detection range 50 is imaged in S101 of FIG. 20, the displacement amount is measured in S301. In S301, the displacement dimension Δx and Δy of the out-of-vehicle coil 23 is measured relative to the reference position using the position of the luminous paint 51 from the image. Because the camera 42 is arranged integrally with the vehicle-side coil 33, the center position of the vehicle-side coil 33 in the image is always same as the reference position. For this reason, the displacement amount Δx and Δy can be measured between the reference position and the center position of the out-of-vehicle coil 23 calculated from the luminous paint 51 in the image. The control part 41 which performs the displacement amount measuring process may be equivalent to a displacement amount measuring portion.

Next, the inclination measurement process shown in S303 is conducted, in which the relative inclination Δz between the out-of-vehicle coil 23 and the vehicle-side coil 33 is measured based on the distance signal output from the ultrasonic sensors 45a-45d. The number of the ultrasonic sensors is not limited and may be set suitably for measuring the relative inclination Δz. The ultrasonic sensors 45a-45d may be equivalent to a distance measuring portion, and the control part 41 which performs the inclination measurement process may be equivalent to an inclination measuring portion.

After the displacement amount Δx and Δy and the relative inclination Δz are calculated, it is determined whether at least one of the displacement amount Δx and Δy and the relative inclination Δz is contained in the electric-power transfer stop range Sc in S305. When at least one of the displacement amount Δx and Δy and the relative inclination Δz is contained in the electric-power transfer stop range Sc (Yes at S305), it is determined that it is necessary to stop the non-contact electric-power transfer because the displacement amount Δx and Δy or the relative inclination Δz is large, and the stop signal is transmitted in S307.

In S307, the stop signal is transmitted to the electric-power transfer equipment 32 to stop the non-contact electric-power transfer, since the amount of position gap or inclination is large. When the stop signal is received by the power receiving control part 36 of the electric-power transfer equipment 32, the non-contact electric-power transfer using the battery equipment 31 is stopped similarly to the case where a foreign matter detection signal is received.

In addition, when the stop signal is transmitted, the stop of the non-contact electric-power transfer may be informed to a user by the foreign matter sensing device 40a or the electric-power transfer equipment 32. Thereby, the user is promoted to move the vehicle 30 so that the amount of position gap or inclination between the coils 33 and 23 is reduced.

On the other hand, when both the displacement amount Δx and Δy and the relative inclination Δz are not contained in the electric-power transfer stop range Sc (No at S305), and when at least one of the displacement amount Δx and Δy and the relative inclination Δz is contained in the electric current restriction range Sb (Yes at S309), it is determined that it is required to restrict the charging current, and the electric current limiting signal is transmitted in S311, since the amount of position gap or inclination between the coils 33 and 23 is comparatively large.

In S311, the electric current limiting signal is transmitted to the electric-power transfer equipment 32 to restrict the charging current, since the amount of position gap or inclination is comparatively large. When the electric current limiting signal transmitted in this way is received by the power receiving control part 36 of the electric-power transfer equipment 32, the charging current in the non-contact electric-power transfer using the battery equipment 31 is restricted to become smaller than or equal to a specified value, so the surface temperature of the out-of-vehicle coil 23 is maintained at the steady value.

Then, the limit-time correction treatment is made in S313. In S313, the after-correction prediction temperature Te_b(t) is set up by correcting the basis prediction temperature Te_a(t) according to the limiting value of the charging current on the assumption that the charging current is restricted to the specified value. In addition, the control part 41 which performs the limit-time correction treatment and a no-limit correction treatment to be described below may be equivalent to a first correction portion.

Then, similarly to the third embodiment, an exothermic foreign matter is detected by comparing the absolute value of the subtraction between the after-correction prediction temperature Te_b(t) and the measurement temperature T(t) with the predetermined threshold ΔTth.

When both the displacement amount Δx and Δy and the relative inclination Δz are comparatively small and are not contained in the electric-power transfer stop range Sb (No at S309), the no-limit correction treatment is conducted at S315 where the charging current is not limited. In S315, the increase in the surface temperature of the out-of-vehicle coil 23 is estimated based on the calculated displacement amount Δx and Δy and inclination Δz, and the after-correction prediction temperature Te_b(t) is set by correcting the basis prediction temperature Te_a(t) by the estimated increase so as to raise the prediction temperature, as shown in FIG. 21.

In addition, the electric-power transfer efficiency in the non-contact electric-power transfer is lowered by the position gap and inclination. Therefore, in this case, the charging time becomes long, and the completion time $t_{e1}$ obtained from the basis prediction temperature Te_a(t) will be delayed to the completion time $t_{e2}$ obtained from the after-correction prediction temperature Te_b(t).

Then, similarly to the third embodiment, an exothermic foreign matter is detected by comparing the absolute value of the subtraction between the after-correction prediction temperature Te_b(t) and the measurement temperature T(t) with the predetermined threshold ΔTth.

For example, as shown in FIG. 21, when the measurement temperature $T(t_1)$ becomes high due to the position gap and/or inclination, compared with the case where there is no position gap, the subtraction between the basis prediction temperature $Te\_a(t_1)$ and the measurement temperature $T(t_1)$ may become larger than the threshold δTth, so an exothermic foreign matter may be incorrectly detected.

According to the present embodiment, the measurement temperature $T(t_1)$ is compared with the after-correction prediction temperature $Te\_b(t_1)$ which is corrected according to the position gap and inclination, so the subtraction becomes smaller, thus the incorrect detection of exothermic foreign matter is restricted.

Accordingly, in the foreign matter sensing device 40 concerning the present embodiment, the displacement amount Δx and Δy of the out-of-vehicle coil 23 from the reference position is measured based on the image taken by the camera 42, and the basis prediction temperature Te_a(t) is corrected into the after-correction prediction temperature Te_b(t) based on the displacement amount Δx and Δy.

In the case where the out-of-vehicle coil 23 is deviated from the reference position when the vehicle 30 is stopped, the power transmission efficiency falls and heat generated by the out-of-vehicle coil 23 is increased. However, the prediction temperature Te(t) is corrected according to the displacement amount Δx and Δy, therefore the incorrect detection resulting from the position gap is restricted, and the detection precision of exothermic foreign matter can be raised.

Furthermore, the plural ultrasonic sensors 45a-45d measure the distance between the vehicle-side coil 33 and the out-of-vehicle coil 23, and the inclination Δz of the out-of-vehicle coil 23 relative to the vehicle-side coil 33 is measured based on the measured distance. The prediction temperature Te(t) is corrected based on both the displacement amount Δx and Δy and the inclination Δz.

Since the prediction temperature Te(t) is corrected according to the inclination Δz of the vehicle-side coil 33 relative to the out-of-vehicle coil 23, the incorrect detection resulting from the inclination Δz is restricted, and the detection precision of exothermic foreign matter can be raised.

Moreover, the luminescent luminous paint 51 is applied to a portion of the foreign matter detection range 50 defined by projecting the out-of-vehicle coil 23 in the foreign matter detection range 50, as a positional information indicating part for calculating the relative position of the out-of-vehicle coil 23 to the foreign matter detection range 50. Therefore, the relative position between the foreign matter detection range 50 and the out-of-vehicle coil 23 becomes clear by detecting the luminous paint 51 in the image with the foreign matter detection range 50. For this reason, since the measurement precision of the displacement amount Δx and Δy improves, the correction precision of the prediction temperature Te(t), i.e., the detection precision of exothermic foreign matter, can be raised further.

In particular, since the luminous paint 51 is applied in the foreign matter detection range 50, as the positional information indicating part, even if it is comparatively dark at night etc., the relative position between the foreign matter detection range 50 and the out-of-vehicle coil 23 becomes clear. Thereby, the measurement precision of the displacement amount Δx and Δy can be improved, and the detection precision of exothermic foreign matter can be raised further.

Figure 22A:
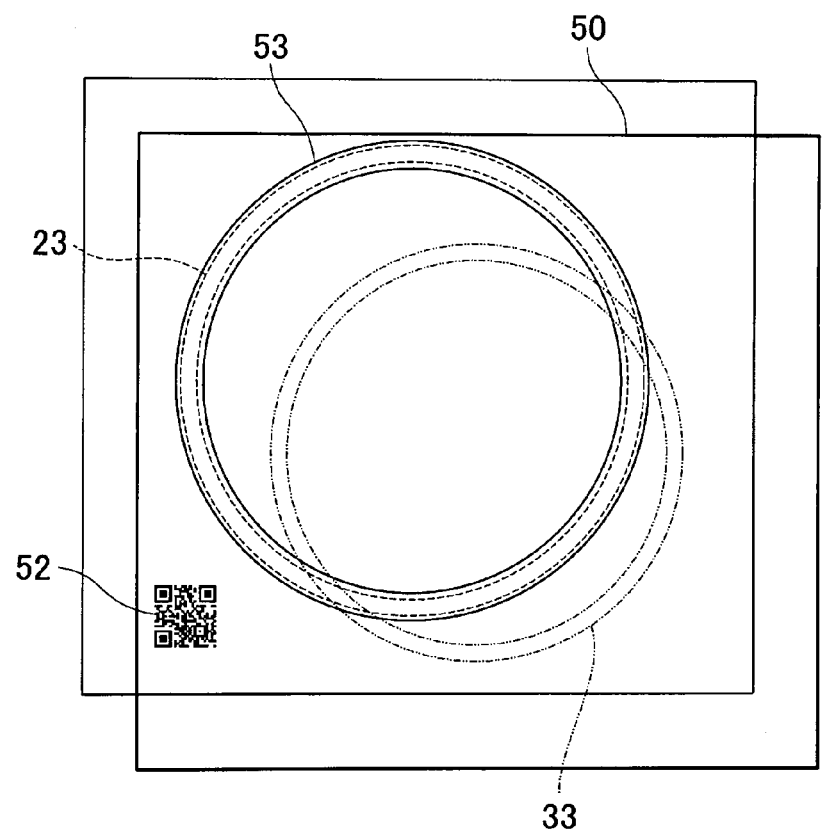
FIGS. 22A and 22B are explanatory drawings illustrating a modification example of the fifth embodiment.
Figure 22B:
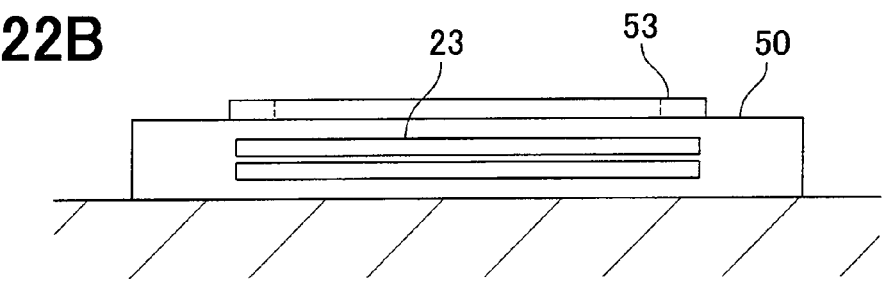

FIGS. 22A and 22B are explanatory drawings illustrating a modification example of the fifth embodiment. FIG. 22A illustrates the foreign matter detection range 50 seen from the side of the vehicle-side coil 33, and FIG. 22B illustrates the foreign matter detection range 50 along the road surface direction.

As shown in FIG. 22A, as a first modification of the fifth embodiment, the foreign matter detection range 50 may have an information code 52 as a positional information indicating part for obtaining the relative position relative to the out-of-vehicle coil 23. The information code 52 may be an optically-read information about the relative position of the out-of-vehicle coil 23 to the foreign matter detection range 50. The information code 52 may be a one-dimensional code such as bar code, or a two-dimensional code such as QR Code (registered trademark).

Thereby, the relative position between the foreign matter detection range 50 and the out-of-vehicle coil 23 becomes clear only by optically reading the information code 52 contained in the image taken by the camera 42. Thereby, the measurement precision of the displacement amount Δx and Δy can be improved, and the detection precision of exothermic foreign matter can be raised further.

Moreover, as shown in FIGS. 22A and 22B, as a second modification of the fifth embodiment, the foreign matter detection range 50 has an annular indicating part 53 as a positional information indicating part for obtaining the relative position relative to the out-of-vehicle coil 23. The annular indicating part 53 has a convex shape protruding from the foreign matter detection range 50, and corresponds to an area defined by projecting the out-of-vehicle coil 23 to the foreign matter detection range 50.

In this case, because the relative position between the foreign matter detection range 50 and the out-of-vehicle coil 23 becomes clear by the image taken by the camera 42, the measurement precision of the displacement amount Δx and Δy can be improved, and the detection precision of exothermic foreign matter can be raised further. Alternatively, the annular indicating part 53 may be constructed by an annular recess having a concave shape.

The fifth embodiment, in which the prediction temperature Te(t) is corrected according to the displacement amount Δx and Δy and/or the inclination Δz, may be applied to other embodiment except sixth and seventh embodiments.

(Sixth Embodiment)

Figure 23:
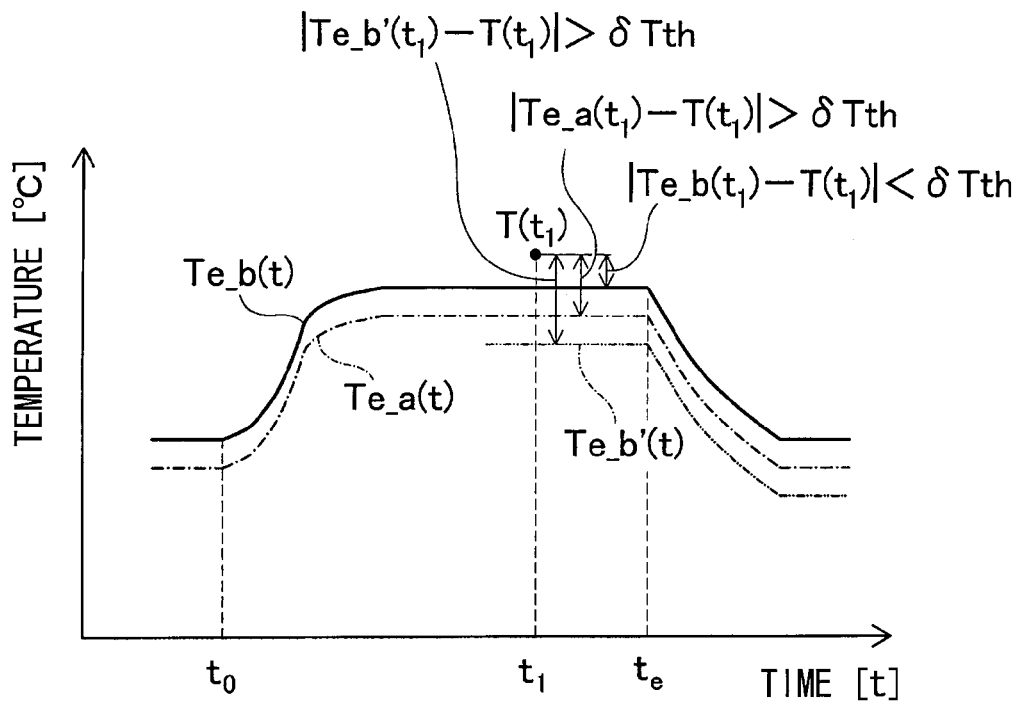
FIG. 23 is a graph illustrating a relationship between a basis prediction temperature and a corrected prediction temperature according to a sixth embodiment.

A foreign matter sensing device and a non-contact electric-power transfer system concerning a sixth embodiment are explained with reference to FIG. 23. FIG. 23 is an explanatory drawing illustrating a relationship between the after-correction prediction temperature Te_b(t) and the basis prediction temperature Te_a(t) in the sixth embodiment.

In the sixth embodiment, the detection precision of exothermic foreign matter is raised by correcting the prediction temperature Te(t) according to an outside air temperature. The substantially same parts and components as the third embodiment are indicated with the same reference numeral and the same description will not be reiterated.

When the outside air temperature becomes high, for example, in summer, the temperature of the foreign matter detection range 50 also becomes comparatively high according to the outside air temperature. When the outside air temperature becomes low in winter, the temperature of the foreign matter detection range 50 also becomes comparatively low according to the outside air temperature. When the prediction temperature Te(t) set in advance with the predetermined temperature is compared with the measurement temperature T(t) of the foreign matter detection range 50 which changes according to the outside air temperature, an exothermic foreign matter may be incorrectly detected if the outside air temperature is comparatively high, or the detection of exothermic foreign matter may be delayed if the outside air temperature is comparatively low.

In the foreign matter detection process of the present embodiment, the outside air temperature is measured using the temperature sensor 43, and the prediction temperature Te(t) is corrected according to the measured outside air temperature. Specifically, as shown in FIG. 23, when the outside air temperature is high, the basis prediction temperature Te_a(t) is corrected to become higher to define the after-correction prediction temperature Te_b(t). Thereby, even if the outside air temperature is high, incorrect detection of exothermic foreign matter is restricted. The control part 41 which corrects the prediction temperature Te(t) according to the outside air temperature may be equivalent to a second correction portion.

Furthermore, when the outside air temperature has a large change during the non-contact electric-power transfer, the after-correction prediction temperature Te_b(t) can be corrected further according to the change in the outside air temperature. For example, when the outside air temperature becomes low during the non-contact electric-power transfer, as shown in FIG. 23, the after-correction prediction temperature Te_b(t) is further corrected into another after-correction prediction temperature Te_b'(t) according to the change in the outside air temperature. Therefore, even if the outside air temperature is lowered, delay in the detection of exothermic foreign matter can be restricted.

Thus, the prediction temperature Te(t) is corrected according to the outside air temperature, thereby restricting the incorrect detection of exothermic foreign matter and the delay in the detection of exothermic foreign matter resulting from the change in the outside air temperature.

The outside air temperature may be measured by other sensor other than the temperature sensor 43. The temperature sensor 43 and the other temperature sensor may be equivalent to an outside air temperature sensor.

The sixth embodiment may be applied to other embodiment except the fifth and seventh embodiments.

(Seventh Embodiment)

Figure 24:
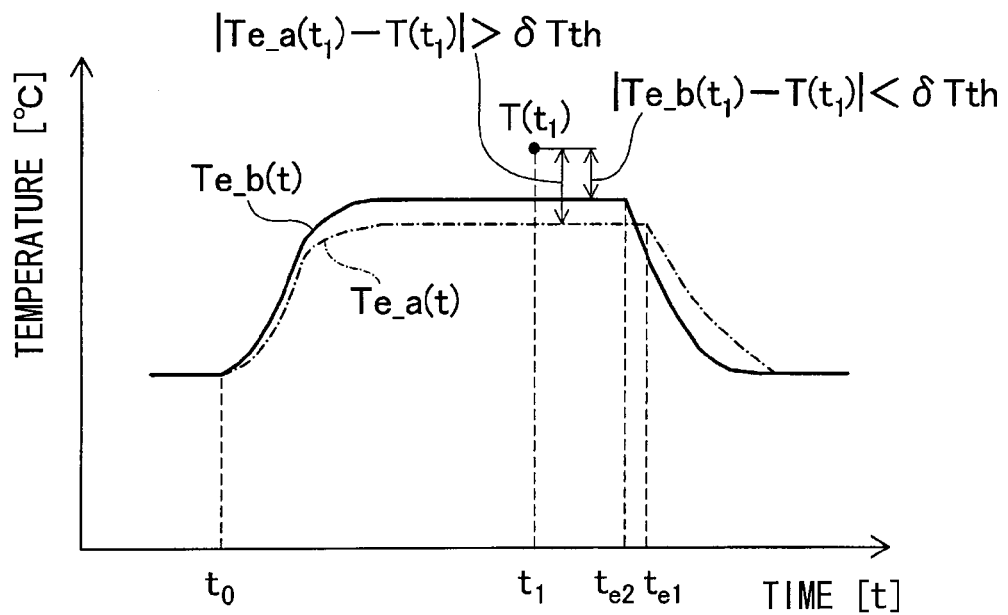
FIG. 24 is a graph illustrating a relationship between a basis prediction temperature and a corrected prediction temperature according to a seventh embodiment.

A foreign matter sensing device and a non-contact electric-power transfer system concerning a seventh embodiment are explained with reference to FIG. 24. FIG. 24 is an explanatory drawing illustrating a relationship between the after-correction prediction temperature Te_b(t) and the basis prediction temperature Te_a(t) in the seventh embodiment.

In the seventh embodiment, the detection precision of an exothermic foreign matter is raised by correcting the prediction temperature Te(t) according to the amount of electric-power transfer when the non-contact electric-power transfer is conducted. The substantially same parts and components as the third embodiment are indicated with the same reference numeral and the same description will not be reiterated.

The charging current becomes comparatively large when the amount of electric-power transfer is large, so the heat generation amount of the out-of-vehicle coil 23 becomes large, and the temperature of the foreign matter detection range 50 also becomes comparatively high. In contrast, the charging current becomes comparatively low when the amount of electric-power transfer is small, so the heat generation amount of the out-of-vehicle coil 23 becomes small, and the temperature of the foreign matter detection range 50 also becomes comparatively low.

Thus, when the temperature of the foreign matter detection range 50 which changes according to the amount of electric-power transfer is compared with the prediction temperature set in advance with assumption of a predetermined electric-power transfer amount, if the amount of electric-power transfer is comparatively small, an exothermic foreign matter may be incorrectly detected. Further, if the amount of electric-power transfer is comparatively large, the detection of exothermic foreign matter may be delayed.

According to the seventh embodiment, the prediction temperature Te(t) is corrected according to the comparison result between the amount of electric-power transfer detected by the monitoring unit 31b and a basis usual amount of electric-power transfer (henceforth referred as a reference transfer amount). Specifically, when the detected amount of electric-power transfer becomes comparatively larger than the reference transfer amount, as shown in FIG. 24, the basis prediction temperature Te_a(t) with the reference transfer amount is corrected to increase as the after-correction prediction temperature Te_b(t). In this case, since the charging time becomes short, the charging complete timing $t_{e2}$ obtained from the after-correction prediction temperature Te_b(t) becomes earlier than the charging complete timing $t_{e1}$ obtained from the basis prediction temperature Te_a(t).

In contrast, when the detected amount of electric-power transfer becomes comparatively smaller with respect to the reference transfer amount, the basis prediction temperature Te_a(t) is corrected to decrease as the after-correction prediction temperature Te_b(t). In this case, since the charging time becomes long, the charging complete timing $t_{e2}$ obtained from the after-correction prediction temperature Te_b(t) becomes later than the charging complete timing $t_{e1}$ obtained from the basis prediction temperature Te_a(t).

Thus, the detection delay or incorrect detection of exothermic foreign matter resulting from the change in the amount of electric-power transfer can be restricted by correcting the prediction temperature Te(t) according to the amount of electric-power transfer. The control part 41 which corrects the prediction temperature Te(t) according to the amount of electric-power transfer may be equivalent to a third correction portion. The amount of electric-power transfer may be measured by other sensor other than the monitoring unit 31b.

The seventh embodiment may be applied to other embodiment except the fifth and sixth embodiments.

(Eighth Embodiment)

Figure 25:
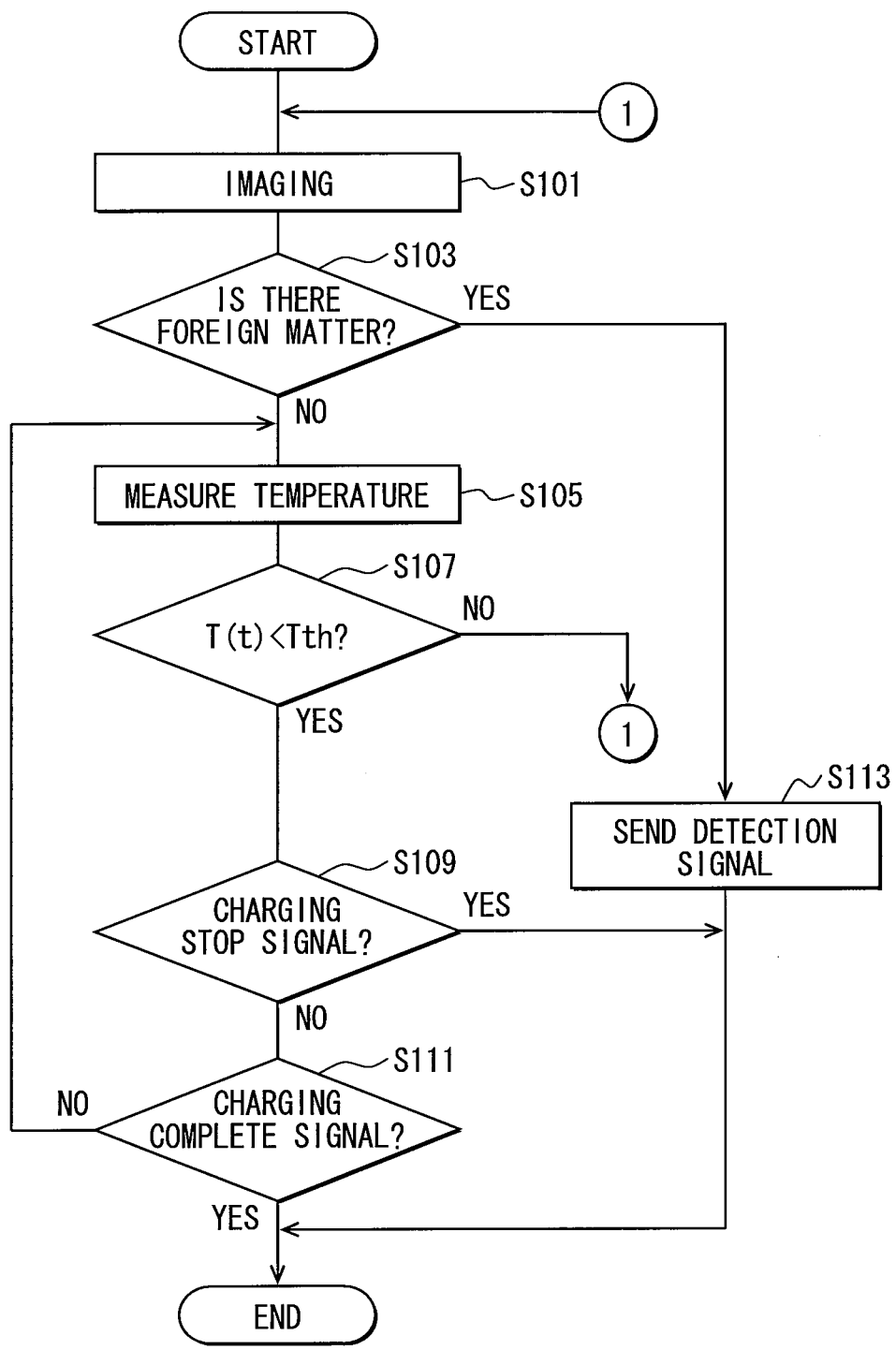
FIG. 25 is a flow chart illustrating a foreign matter detection process according to an eighth embodiment.

A foreign matter sensing device and a non-contact electric-power transfer system concerning an eighth embodiment are explained with reference to FIG. 25. FIG. 25 is a flow chart illustrating a foreign matter detection process of the eighth embodiment.

The foreign matter sensing device 40 of the eighth embodiment differs from the first embodiment at the point carrying out the foreign matter detection process based on the flow chart shown in FIG. 25 instead of FIG. 3, in order to reduce the incorrect detection of exothermic foreign matter. The substantially same parts and components as the first embodiment are indicated with the same reference numeral and the same description will not be reiterated.

In the present embodiment, when it is determined that there is an exothermic foreign matter according to the measurement temperature T(t) of the foreign matter detection range 50, the existence of foreign matter is determined again based on the image of the foreign matter detection range 50 taken by the camera 42, in order to reduce the incorrect detection of exothermic foreign matter.

Specifically, as shown in the flow chart of FIG. 25, when the measurement temperature T(t) is more than or equal to the temperature threshold Tth (No at S107), the foreign matter detection process will be started again from S101. In this case, when an exothermic foreign matter is actually existing in the foreign matter detection range 50, the exothermic foreign matter is contained in the image taken by the camera in S101 (Yes at S103), and the foreign matter detection signal is output in S113.

In contrast, the temperature of the foreign matter detection range 50 is raised to be more than the temperature threshold Tth by other factor other than the exothermic foreign matter (No at S107), an exothermic foreign matter is not contained in the foreign matter image (No at S103), S105 is executed again without transmitting the foreign matter detection signal.

For example, the other factor may be a small animal or cigarette end (tobacco butt) in the foreign matter detection range 50. The control part 41 which carries out S103 after it is determined as No at S107 may be equivalent to an example of a third determiner. In addition, the third determiner may determine whether the foreign matter is contained in the image of the foreign matter detection range 50 taken by other camera mounted to the non-contact electric-power transfer equipment 20 other than the camera 42 after it is determined as No at S107.

Thus, when it is determined that there is a foreign matter according to the measurement temperature T(t), the foreign matter detection range 50 will be imaged as a foreign matter detection picture with the camera 42, and the existence of the foreign matter in the foreign matter detection range 50 will be determined based on this foreign matter detection picture. Since the existence of foreign matter is determined based on the foreign matter detection picture in the state where the existence of foreign matter is presumed, incorrect detection of exothermic foreign matter can be reduced.

In addition, when the measurement temperature T(t) is determined to be more than the temperature threshold Tth (No at S107), and when an exothermic foreign matter is not contained in the foreign matter detection picture (No at S103) continuously for a predetermined time continuation, the foreign matter detection signal or the similar signal may be transmitted to the power receiving control part 36 of the electric-power transfer equipment 32.

The eighth embodiment may be applied to other embodiment.

(Ninth Embodiment)

Figure 26:
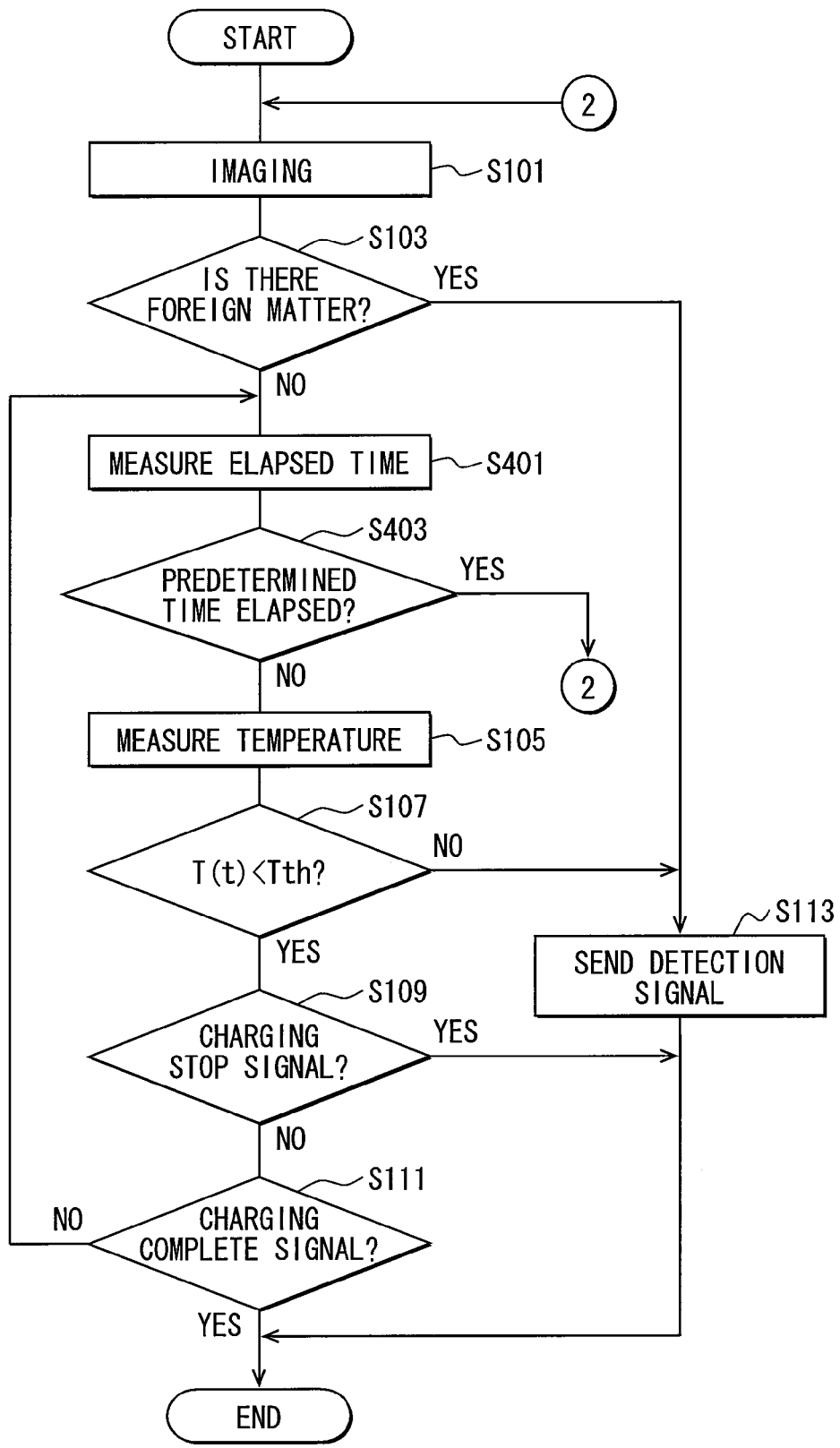
FIG. 26 is a flow chart illustrating a foreign matter detection process according to a ninth embodiment.

A foreign matter sensing device and a non-contact electric-power transfer system concerning a ninth embodiment are explained with reference to FIG. 26. FIG. 26 is a flow chart illustrating a foreign matter detection process of the ninth embodiment.

The foreign matter sensing device 40 of the ninth embodiment differs from the first embodiment at the point carrying out the foreign matter detection process based on the flow chart shown in FIG. 26 instead of FIG. 3, in order to raise the detection accuracy of foreign matter. The substantially same parts and components as the first embodiment are indicated with the same reference numeral and the same description will not be reiterated.

In the present embodiment, in order to raise the detection accuracy of foreign matter, the foreign matter detection range 50 is intermittently imaged with the camera 42 as an intermittent picture, whenever a predetermined time (henceforth intermittent time) passes, and the existence of the foreign matter in the foreign matter detection range 50 is determined based on the intermittent picture.

Specifically, as shown in the flow chart of FIG. 26, when it is determined that a foreign matter is not imaged (No at S103), the elapsed time from the determination is started to count at S401. That is, the time period elapsed after it is determined that a foreign matter is not imaged is measured at S401. Then, at S403, it is determined whether the elapsed time exceeds a predetermined intermittent time. If the elapsed time has not passed the predetermined intermittent time (No at S403), S105-S111 is repeated so as to detect an exothermic foreign matter by comparing the measurement temperature T(t) with the temperature threshold Tth.

When the state where the measurement temperature T(t) is lower than the temperature threshold Tth continues and when the elapsed time passes the predetermined intermittent time (Yes at S403), the existence of foreign matter will be determined based on the image of the foreign matter detection range 50 taken in S101. If it is determined that the foreign matter is not contained in the image (No at S103), S401 is executed, and the elapsed time count will be started again after the already elapsed time is cleared. In addition, the control part 41 which carries out S403 may be equivalent to an example of a fourth determiner.

Thus, the existence of the foreign matter in the foreign matter detection range 50 is intermittently determined based on the intermittent picture. Accordingly, the detection accuracy of foreign matter can be raised by detecting the foreign matter in the foreign matter detection range 50 not only according to the measurement temperature T(t), but also according to the intermittent picture taken by the camera 42.

The ninth embodiment may be applied to other embodiment.

(Tenth Embodiment)

Figure 27:
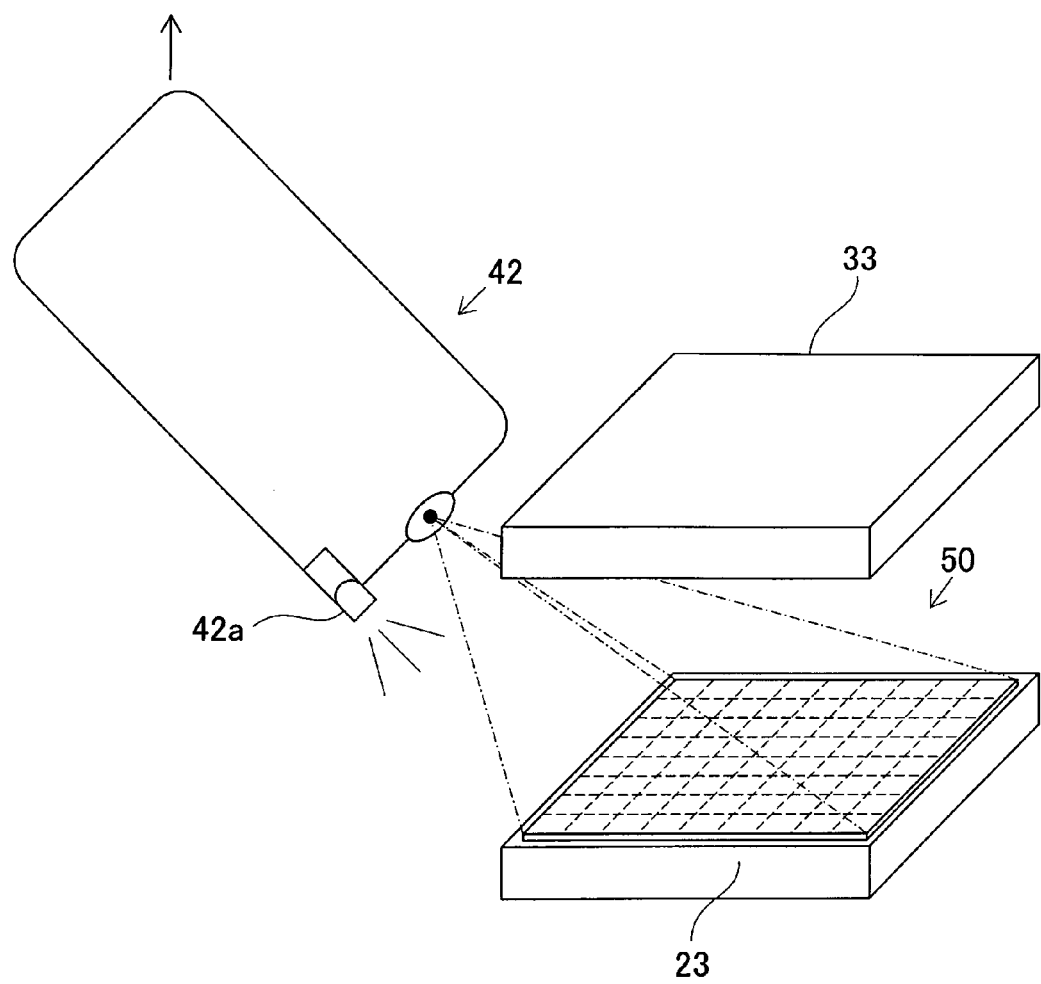
FIG. 27 is an explanatory drawing illustrating a foreign matter detecting device according to a tenth embodiment.

A foreign matter sensing device and a non-contact electric-power transfer system concerning a tenth embodiment are explained with reference to FIG. 27. FIG. 27 illustrates the foreign matter sensing device 40 of the tenth embodiment which differs from the foreign matter sensing device of the first embodiment at the point which newly adopts a light source equipment 42a so that the foreign matter detection range 50 can be imaged even if it is dark around the foreign matter detection range 50.

As shown in FIG. 27, the foreign matter sensing device 40 of the present embodiment has the light source equipment 42a as a lighting portion which can irradiate light to the foreign matter detection range 50. The light source equipment 42a is mounted to the camera 42. Thereby, even if the electric-power transfer is conducted in night where the foreign matter detection range 50 becomes dark, the foreign matter detection range 50 can be imaged with the camera 42 using the light emitted from the light source equipment 42a.

The tenth embodiment may be applied to other embodiment.

The present disclosure is not limited to the above embodiments, and may be modified as follows.

The foreign matter sensing device 40, 40a may be constructed to have an air sending portion which blows away the detected foreign matter using a compressed air, for example. Specifically, a foreign matter sensing device which detects a foreign matter intervening between the vehicle-side coil used when the battery equipment mounted to the vehicle is charged and discharged, and the out-of-vehicle coil which performs the non-contact electric-power transfer to the vehicle-side coil includes an imaging portion, a first determiner, a temperature sensor, a second determiner, and an air sending portion. The imaging portion images the foreign matter detection range above the out-of-vehicle coil. The first determiner determines the existence of the foreign matter in the foreign matter detection range based on the image imaged by the imaging portion. The temperature sensor senses an ambient temperature around the foreign matter detection range. The second determiner determines the existence of the foreign matter in the foreign matter detection range based on the measurement temperature measured by the temperature sensor. The air sending portion sends air to the foreign matter detection range. When at least one of the first determiner and the second determiner determines that there is a foreign matter in the foreign matter detection range, the air sending portion sends air to the foreign matter detection range.

The air sending portion operates to blow away the foreign matter in the foreign matter detection range if the foreign matter is detected according to the image or the measurement temperature in the foreign matter detection range. Therefore, the non-contact electric-power transfer can be continued after blowing away the foreign matter from the foreign matter detection range.

The electric-power transfer equipment 32 can send electric power from the rechargeable battery unit 31a of the battery equipment 31 to an external equipment through the vehicle-side coil 33. In this case, the foreign matter sensing device 40 can detect a foreign matter in a protection area (corresponding to the foreign matter detection range) which protects the coil at a position above the coil located to oppose the vehicle-side coil 33.

The out-of-vehicle coil 23 may be arranged on the road surface, and at least a part of the out-of-vehicle coil 23 may be laid under the road surface, so as to counter the vehicle-side coil 33 of the vehicle 30 which is parked.

The non-contact electric-power transfer equipment 20 may be installed in a place where the vehicle 30 may be parked other than the predetermined parking space.

Such changes and modifications are to be understood as being within the scope of the present disclosure as defined by the appended claims.

What is claimed is:

1. A foreign matter sensing device that detects a foreign matter between a vehicle-side coil, which is used when a battery equipment mounted to a vehicle is charged and discharged, and an out-of-vehicle coil which performs a non-contact electric-power transfer with the vehicle-side coil, the foreign matter sensing device comprising:
    an imaging portion that imaging an image of a foreign matter detection range above the out-of-vehicle coil;
    a first determiner that determines whether there is a foreign matter in the foreign matter detection range based on the image imaged by the imaging portion;
    a temperature sensor sensing a temperature of the foreign matter detection range; and
    a second determiner that determines whether there is a foreign matter in the foreign matter detection range based on the temperature sensed by the temperature sensor, wherein
    the first determiner determines whether there is a foreign matter in the foreign matter detection range in response to a start demand instructing to start transferring electric-power,
    the second determiner executes determining whether there is a foreign matter in the foreign matter detection range while electric-power is transferred between the vehicle-side coil and the out-of-vehicle coil, after the first determiner determines that there is no foreign matter;
    the second determiner determines whether there is a foreign matter in the foreign matter detection range by comparing the temperature sensed by the temperature sensor with a prediction temperature of the foreign matter detection range assumed while the non-contact electric-power transfer is performed;
    the foreign matter sensing device further comprises:
    a position displacement measuring portion that measures a position displacement of the out-of-vehicle coil from a reference position based on the image imaged by the imaging portion, the reference position being defined by a relative position of the out-of-vehicle coil relative to the vehicle-side coil at which a power transmission efficiency of the non-contact electric-power transfer becomes the maximum; and
    a first correction portion that corrects the prediction temperature based on the position displacement of the out-of-vehicle coil measured by the position displacement measuring portion.

2. The foreign matter sensing device according to claim 1, wherein
    the foreign matter detection range is divided into a plurality of detection areas,
    the temperature sensor senses temperature in at least two detection areas of the plurality of detection areas, and
    the second determiner determines whether there is a foreign matter based on the temperature in the at least two detection areas.

3. The foreign matter sensing device according to claim 1, wherein
    the foreign matter detection range is larger than a range of a road surface overlapping with the vehicle-side coil.

4. The foreign matter sensing device according to claim 1, wherein
    at least two of the vehicle-side coils are arranged along a road surface direction, and at least two of the out-of-vehicle coils are arranged along the road surface direction, and
    the foreign matter detection range is set to include the at least two of the out-of-vehicle coils that transfer electric-power with the vehicle-side coils.

5. The foreign matter sensing device according to claim 1, wherein
    the second determiner determines that there is a foreign matter when a variation amount of the temperature sensed by the temperature sensor is larger than or equal to a variation threshold value at which the foreign matter is assumed to generate heat.

6. The foreign matter sensing device according to claim 1, further comprising:
    at least two distance measuring portions that measure a distance between the vehicle-side coil and the out-of-vehicle coil; and
    an inclination measuring portion that measures an inclination of the out-of-vehicle coil relative to the vehicle-side coil based on the distance measured by the at least two distance measuring portions, wherein
    the first correction portion corrects the prediction temperature based on the position displacement of the out-of-vehicle coil measured by the position displacement measuring portion and the inclination of the out-of-vehicle coil measured by the inclination measuring portion.

7. The foreign matter sensing device according to claim 1, wherein
    the foreign matter detection range has a positional information indicating part that indicates a positional information for determining a relative position of the out-of-vehicle coil relative to the foreign matter detection range.

8. The foreign matter sensing device according to claim 7, wherein
the positional information indicating part is a luminous paint applied to an overlap range of the out-of-vehicle coil overlapping with the foreign matter detection range.

9. The foreign matter sensing device according to claim 7, wherein
the positional information indicating part is an optically-readable information code relating to the relative position of the out-of-vehicle coil relative to the foreign matter detection range.

10. The foreign matter sensing device according to claim 7, wherein
the positional information indicating part is defined by forming an overlap range of the out-of-vehicle coil overlapping with the foreign matter detection range into a convex or concave shape relative to a surrounding range surrounding the overlap range.

11. The foreign matter sensing device according to claim 1, further comprising:
an outside air temperature sensor sensing a temperature of outside air; wherein
the correction portion corrects the prediction temperature based on the temperature of outside air sensed by the outside air temperature sensor.

12. The foreign matter sensing device according to claim 1, wherein:
the correction portion corrects the prediction temperature in accordance with an electric-power transfer amount while the non-contact electric-power transfer is performed.

13. The foreign matter sensing device according to claim 1, further comprising:
an alarming portion which reports an alarm information informing a presence of the foreign matter when the first determiner or the second determiner determines that there is the foreign matter.

14. The foreign matter sensing device according to claim 13, wherein
the imaging portion images the foreign matter detection range as a foreign matter detection image, when it is determined that there is the foreign matter, and
the alarm information includes the foreign matter detection image.

15. The foreign matter sensing device according to claim 1, wherein the imaging portion images the foreign matter detection range as a foreign matter detection image when it is determined that there is the foreign matter, the foreign matter sensing device further comprising:
a third determiner that determines whether there is a foreign matter in the foreign matter detection range based on the foreign matter detection image imaged by the imaging portion.

16. The foreign matter sensing device according to claim 1, wherein the imaging portion intermittently images the foreign matter detection range as an intermittent image, the foreign matter sensing device further comprising:
a third determiner that determines whether there is a foreign matter in the foreign matter detection range based on the intermittent image imaged by the imaging portion.

17. The foreign matter sensing device according to claim 1, further comprising:
a lighting portion that emits a light to the foreign matter detection range.

18. The foreign matter sensing device according to claim 1, wherein
the temperature sensor is an infrared sensor which senses the temperature of the foreign matter detection range by detecting an infrared light from the foreign matter detection range.

19. The foreign matter sensing device according to claim 18, wherein
the infrared sensor is one of a plurality of infrared sensors.

20. A non-contact electric-power transfer system comprising:
the foreign matter sensing device according to claim 1;
the out-of-vehicle coil; and
a control part that controls the non-contact electric-power transfer using the battery equipment through the out-of-vehicle coil and the vehicle-side coil.

21. The non-contact electric-power transfer system according to claim 20, wherein
the control part stops the non-contact electric-power transfer when the foreign matter sensing device detects a foreign matter.

22. The foreign matter sensing device according to claim 1, wherein
the second determiner determines whether there is a foreign matter in the foreign matter detection range based on the temperature sensed by the temperature sensor without lighting a space between the out-of-vehicle coil and the vehicle-side coil only after the first determiner finishes determining that there is no foreign matter in the foreign matter detection range.

23. A foreign matter sensing device configured to detect a foreign matter between a vehicle-side coil, which is used when a battery equipment mounted to a vehicle is charged and discharged, and an out-of-vehicle coil which performs a non-contact electric-power transfer with the vehicle-side coil, the foreign matter sensing device comprising:
a control unit, including a microcomputer and storage memory, the control unit configured to:
receive image data corresponding to an image of a foreign matter detection range proximate to the out-of-vehicle coil;
conduct a first determination of whether there is foreign matter in the foreign matter detection range based on the received image data in response to a start command instructing to start transfer of electric-power;
receive temperature data corresponding to a temperature of the foreign matter detection range;
conduct a second determination of whether there is foreign matter in the foreign matter detection range based on received temperature data while electric-power is transferred between the vehicle-side coil and the out-of-vehicle coil and after the first determination determines that there is no foreign matter in the foreign matter detection range; wherein the second determination determines whether there is a foreign matter in the foreign matter detection range by comparing the temperature corresponding to the received temperature data with a prediction temperature of the foreign matter detection range assumed while the non-contact electric-power transfer is performed;
measure a position displacement of the out-of-vehicle coil from a reference position based on the image corresponding to the received image data, the reference position being defined by a relative position of the out-of-vehicle coil relative to the vehicle-side coil at which a power transmission efficiency of the non-contact electric-power transfer becomes the maximum; and correct the prediction temperature based on the measured position displacement of the out-of-vehicle coil.

* * * * *